US009023991B2

(12) United States Patent
Sarasa Barrio

(10) Patent No.: US 9,023,991 B2
(45) Date of Patent: May 5, 2015

(54) ALBUMIN-AMYLOID PEPTIDE CONJUGATES AND USES THEREOF

(75) Inventor: J. Manuel Sarasa Barrio, Saragossa (ES)

(73) Assignee: Araclon Biotech B.L., Saragossa (ES)

(*) Notice: Subject to any disclaimer, the term of this patent is extended or adjusted under 35 U.S.C. 154(b) by 0 days.

(21) Appl. No.: 13/322,417

(22) PCT Filed: May 26, 2010

(86) PCT No.: PCT/EP2010/057235
§ 371 (c)(1),
(2), (4) Date: Feb. 8, 2012

(87) PCT Pub. No.: WO2010/136487
PCT Pub. Date: Dec. 2, 2010

(65) Prior Publication Data
US 2012/0130049 A1 May 24, 2012

(30) Foreign Application Priority Data

May 26, 2009 (EP) ..................................... 09382078

(51) Int. Cl.
*C07K 7/06* (2006.01)
*A61K 39/00* (2006.01)
*A61K 47/48* (2006.01)

(52) U.S. Cl.
CPC ............... *C07K 7/06* (2013.01); *A61K 39/0007* (2013.01); *A61K 47/48284* (2013.01); *A61K 47/4833* (2013.01); *A61K 2039/6081* (2013.01)

(58) Field of Classification Search
CPC ... A61K 38/00; A61K 39/00; A61K 39/0006; A61K 2039/6081; C07K 2319/00; C07K 14/765
USPC ......................................... 424/185.1; 530/362
See application file for complete search history.

(56) References Cited

U.S. PATENT DOCUMENTS

| | | | |
|---|---|---|---|
| 5,955,317 A | 9/1999 | Suzuki et al. | |
| 6,787,637 B1 | 9/2004 | Schenk et al. | |
| 6,926,898 B2* | 8/2005 | Rosen et al. | 424/192.1 |
| 7,427,392 B1 | 9/2008 | Seubert | |
| 2007/0098721 A1 | 5/2007 | Hillen et al. | |
| 2007/0172496 A1 | 7/2007 | Olsen | |
| 2009/0162362 A1* | 6/2009 | Sarasa Barrio | 424/139.1 |

FOREIGN PATENT DOCUMENTS

| | | | |
|---|---|---|---|
| EP | 1308461 A2 * | 5/2003 | |
| EP | 0906577 B1 | 9/2008 | |
| WO | WO 98/44955 A1 | 10/1998 | |
| WO | WO 2004/018997 A2 | 3/2004 | |
| WO | WO 2004/098631 A1 | 11/2004 | |

OTHER PUBLICATIONS

Alon Monsonego, Ruth Maron, Victor Zota, Dennis J. Selkoe, and Howard Weiner. Immune hyporesponsiveness to amyloid b-peptide in amyloid precursor protein transgenic mice: Implications for the pathogenesis and treatment of Alzheimer's disease. Aug. 8, 2001. PNAS. 98(18); 10273-10278.*
Einar M Sigurdsson, et al. An Attenuated Immune Response is Sufficient to Enhance Cognition in an Alzheimer's Disease Mouse Model Immunized with Amyloid-b Derivatives. Jul. 14, 2004. The Journal of Neuroscience. 24(28):6277-6282.*
Adriana A Reyes Barcelo, et al. Soluble aggregates of the amyloid-b peptide are trapped by serum albumin to enhance amyloid-b activation of endothelial cells. Apr. 27, 2009. Journal of Biological Engineering. 3(5):1-8.*
European Patent Application EP1 308 461 A2 (Takeda Chemical Industries Ltd. [JP]); published May 7, 2003.
Mar. 24, 2011 International Preliminary Report on Patentability in PCT International application No. PCT/EP2010/057235, filed May 26, 2010.
Bloom J.K. et al., "Abetal-10 and Abetal-15 Coupled With KLH or BSA Yields Anti-Beta Antibody Levels" Society for Neuroscience Abstract Viewer and Itinerary Planner, vol. 2003, XP00811735 & 33rd Annual Meeting of the Society of Neuroscience; New Orleans, LA, USA; Nov. 8-12, 2003.
Coligan J.E. et al., "Production of Antipeptide Antisera", Current Protocols in Neuroscience/Editorial Board, Jacqueline N. Crawley ... [et al.] May 2001, vol. chapter 5, May 2001, page Unit 5.6, XP002545043.
Monsonego, A. et al., "Immune Hyporesponsiveness to Amyloid Beta-Peptide in Amyloid Precursor Protein Transgenic Mice: Implications for the Pathogenesis and Treatment of Alzheimer's Disease", Proceedings of the National Academy of Sciences of USA, National Academy of Science, Washington, DC, US, vol. 98, No. 18, Aug. 28, 2001, pp. 10273-10278, XP001153418.
Ida, N. et al., "Analysis of Heterogeneous βA4 Peptides in Human Cerebrospinal Fluid and Blood by a Newly Developed Sensitive Western Blot Assay", The Journal of Biological Chemistry, vol. 271, No. 37, Issue of Sep. 13, 1996, pp. 22908-22914, 1996.
PCT International Application Publication No. WO 2005/072777 (Curix Aps [DK]; Olesen Ole Frilev [DK]; Birkelund Andersen Svend [DK]); published Aug. 11, 2005, of PCT International Application No. PCT/DK2005/000067, filed Jan. 28, 2005.
PCT International Application Publication No. WO 2006/121656 (Merck & Co Inc. [US]; Garsky Victor M [US]; Joyce Joseph G [US]; Keller) published Nov. 16, 2006, of PCT International Application No. PCT/US2006/016481, filed May 1, 2006.
Bloom J K et al., "Abetal-10 and Abetal-15 couples with KLH or BSA yields anti-Abeta antibody levels.", Society for Neuroscience Abstract Viewer and Itinerary Planner, vol. 2003.

(Continued)

*Primary Examiner* — David J Steadman
*Assistant Examiner* — Paul Holland
(74) *Attorney, Agent, or Firm* — Gary J. Gershik; Cooper & Dunham LLP

(57) ABSTRACT

The invention provides conjugates comprising albumin and a peptide derived from the C-terminal region of amyloid beta peptide, as well as uses thereof for the treatment of diseases characterized by the deposition of amyloid proteins and, in particular, for the treatment of Alzheimer's disease.

6 Claims, 7 Drawing Sheets

(56) References Cited

OTHER PUBLICATIONS

Coligan J E et al., "Production of antipeptide antisera." Current Protocols in Neuroscience/Editorial Board, Jacquelin N. Crawley . . . [et al.] May 2001, vol. Chapter 5, May 2001.
Monsonego A et al., "Immune Hyporesponsiveness to Amyloid Beta-Peptide in Amyloid Precursor Protein Transgenic Mice: Implications for the Pathogenesis and Treatment of Alzheimer's Disease", Proceedings of the National Academy of Sciences of USA, National Academy of Science, Washington, DC, US, vol. 98, No. 18, Aug. 28, 2001, pp. 10273-10278.
International Search Report issued by the International Searching Authority (ISA/O.E.P.M.) on Oct. 8, 2010 in connection With International Application No. PCT/EP2010/057235.

* cited by examiner (A)

(B)

(A)

(B)

ALBUMIN-AMYLOID PEPTIDE CONJUGATES AND USES THEREOF

RELATED APPLICATIONS

This application is a §371 national stage of PCT International Application No. PCT/EP2010/057235, filed May 26, 2010, claiming priority of European Patent Application No. EP 09382078.5, filed May 26, 2009, the contents of each of which are hereby incorporated by reference into this application.

REFERENCE TO SEQUENCE LISTING

This application incorporates-by-reference nucleotide and/or amino acid sequences which are present in the file named "111123_0206_83603_Substitute_Sequence_Listing_GC.txt," which is 13.7 kilobytes in size, and which was created Nov. 23, 2011 in the IBM-PC machine format, having an operating system compatibility with MS-Windows, which is contained in the text file filed Nov. 23, 2011 as part of this application.

FIELD OF THE INVENTION

The invention relates to therapeutic compositions comprising albumin-amyloid peptide conjugates and uses thereof and, more specifically, to its use for the treatment of diseases associated with deposition of amyloid proteins, such as Alzheimer disease.

BACKGROUND OF THE INVENTION

Amyloid diseases or amyloidoses include a number of disease states having a wide variety of outward symptoms. These disorders have in common the presence of abnormal extracellular deposits of protein fibrils, known as "amyloid fibrils", "amyloid deposits" or "amyloid plaques" that are usually about 10-100 nm in diameter and are localized to specific organs or tissue regions. Such plaques are composed primarily of a naturally occurring soluble protein or peptide. These insoluble deposits are composed of generally lateral aggregates of fibrils that are approximately 10-15 nm in diameter. Though diverse in their occurrence, all amyloid deposits have common morphologic properties, stain with specific dyes (e.g. Thioflavin T, Congo red), and have a characteristic red-green birefringent appearance in polarized light after staining.

Amyloid-related diseases are characterized by the type of protein present in the deposit. For example, neurodegenerative diseases such as scrapie, bovine spongiform encephalitis, Creutzfeldt-Jakob disease and the like are characterized by the appearance and accumulation of a protease-resistant form of a prion protein (referred to as AScr or PrP-27) in the central nervous system. Similarly, Alzheimer's disease, another neurodegenerative disorder, is characterized by the deposition of amyloid plaques and neurofibrillary tangles. In this case, the plaque and blood vessel amyloid is formed by the deposition of fibrillar amyloid beta protein. Other diseases such as adult-onset diabetes (Type 11 diabetes) are characterized by the localized accumulation of amyloid in the pancreas.

Each amyloidogenic protein has the ability to fold into beta-sheets and to form insoluble fibrils, which get deposited extracellularly or intracellularly. Each amyloidogenic protein, although different in amino acid sequence, has the same property of forming fibrils and binding to other elements such as proteoglycan, amyloid P and complement component. Moreover, each amyloidogenic protein has amino acid sequences, which, although different, can catalyze the formation of beta-sheet cells. As per example, the amyloid beta fibrils have been associated with dead neuronal cells and microgliosis in patients with Alzheimer's disease. When tested in vitro, the amyloid beta peptide was shown to be capable of triggering an activation process of microglia (brain macrophages), which would explain the presence of microgliosis and brain inflammation found in the brain of patients with Alzheimer's disease.

In another type of amyloidosis seen in patients with Type II diabetes, the amyloidogenic protein IAPP has been shown to induce beta-islet cell toxicity in vitro. Hence, appearance of IAPP fibrils in the pancreas of Type II diabetic patients could contribute to the loss of the beta islet cells (Langerhans) and organ dysfunction.

One of the most prominent amyloid diseases is Alzheimer's disease, which is a progressive neurodegenerative disease affecting approximately 0.5-1% of the total population in the western world. Alzheimer's disease is characterized by the deposition of large numbers of amyloid plaques in the brain. This deposition is assumed to cause the pathology of the disease and most approaches to prevent Alzheimer's disease is aimed at reducing, removing, or preventing the formation of amyloid plaques. The main constituent of the amyloid plaques is the amyloid beta peptide (Aβ), a 40-42 amino-acid protein that is produced through cleavage of the amyloid precursor protein (APP)

The patent application US20070172496 discloses conjugates comprising the Aβ(33-42) peptide, a peptide recognized by a monoclonal antibody and albumin which are used as capture antigens in ELISA assays for determining the presence of anti-Aβ antibodies in a sample from a patient who has been immunized with a complex formed by different peptides derived from Aβ(1-42) peptide and so called ligand-presenting assembly o LPA.

Thus, there is a need in the art for additional immunogenic compositions capable of inducing an effective and sustained decreased in plasma amyloid levels and to reduce the number of amyloid deposits.

SUMMARY OF THE INVENTION

In a first aspect, the invention relates to a conjugate comprising a peptide derived from the C-terminal region of Aβ(1-42) and albumin for use in medicine.

In another aspect, the invention relates to a composition comprising a conjugate comprising a peptide derived from the C-terminal region of Aβ(1-42) and albumin and an adjuvant for use in medicine.

In another aspect, the invention relates to a conjugate comprising at least an immunogenic peptide derived from the C-terminal region of Aβ(1-42) and albumin or a composition comprising at least one immunogenic peptide derived from the C-terminal region of Aβ(1-42) and albumin and an adjuvant, for use in the treatment or prevention of a disease associated with deposition of amyloid proteins.

DETAILED DESCRIPTION OF THE INVENTION

Figure 1:
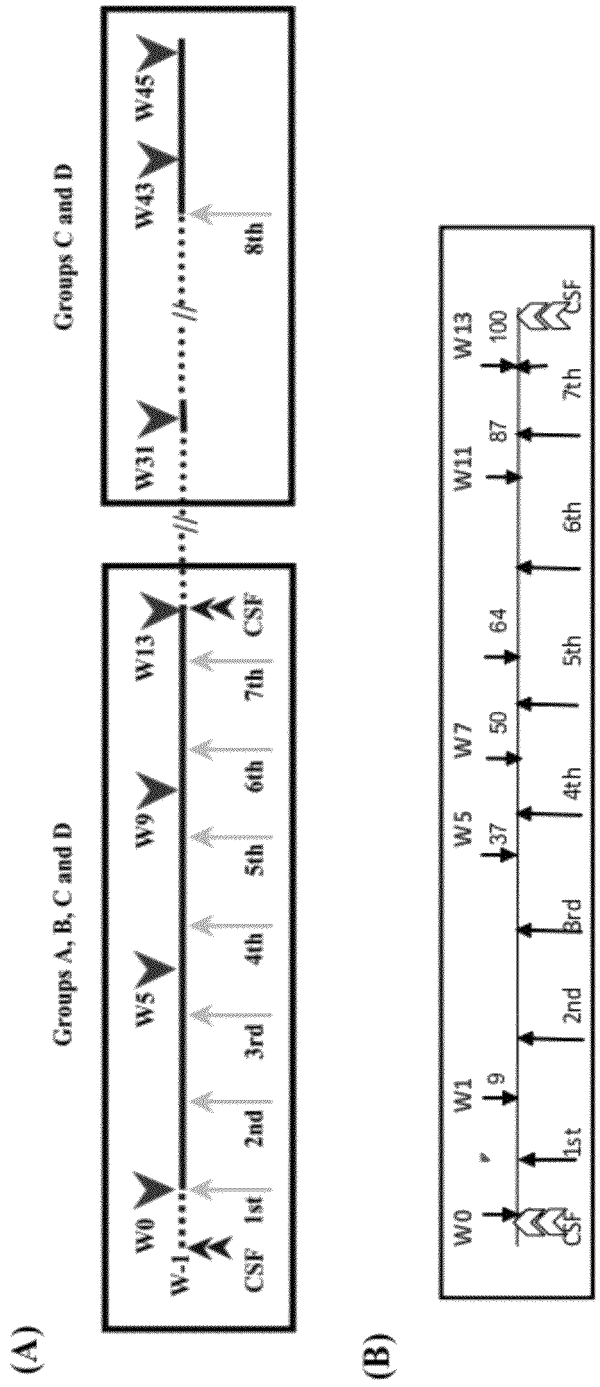
FIG. 1 is a diagram illustrating the schedule of immunization injections of Aβ peptides (arrows on the bottom), indicating the number of immunization below the line, blood sample collection (arrows on the top), indicating the corresponding time point for each sample collection in weeks (W) and CFS sample collection is in week 0 and week 13 (double arrowheads). (A) is the schedule of immunization injections of Aβ (x-42) peptide and (B) of Aβ(x-40) peptide. In (A), the left frame represents the schedule followed by all the animals and the right frame represents the additional interventions affecting only the groups C and D.

Conjugates of the Invention for Use in Medicine

The authors of the present invention have found that the administration of a conjugate comprising a peptide derived the C-terminal region of amyloid beta protein (1-42) [Aβ(1-42)] region and albumin gives rise, surprisingly, to the presence of antibodies against said peptide and to a decrease of serum levels of the proteins Aβ(1-40) and Aβ(1-42), which are the main constituents of the amyloid plaques in Alzheimer's disease. These results open a new therapeutic window for treating, preventing and/or ameliorating diseases associated with deposition of amyloid proteins.

Thus, in one aspect, the invention relates to a conjugate comprising an immunogenic peptide derived from the C-terminal region of Aβ(1-42) and albumin for use in medicine.
Immunogenic Peptide Derived from the C-Terminal Region of Aβ(1-42)

The term "immunogenic peptide" as used herein refers to a peptide which comprises an allele-specific motif, an epitope or other sequence such that the polypeptide or the fragment will bind an MHC molecule and induce a cytotoxic T lymphocyte ("CTL") response, and/or a B cell response (for example, antibody production), and/or T-helper lymphocyte response, and/or a delayed type hypersensitivity (DTH) response against the antigen from which the immunogenic peptide is derived, namely the amyloid beta peptide. Suitable methods for determining whether a given peptide is immunogenic are shown for instance in the examples of the present invention. These methods are based on the ability of said immunogenic peptides to generate anti-amyloid beta antibodies in animals after the administration of said peptides.

The term "amyloid beta peptide" is used herein interchangeably with Abeta, amyloid beta protein, "A beta," "beta AP," "A beta peptide," or "Aβ peptide and refers to a family of peptides that are the principal chemical constituent of the senile plaques and vascular amyloid deposits (amyloid angiopathy) found in the brain in patients of Alzheimer's disease (AD), Down's Syndrome, and Hereditary Cerebral Hemorrhage with Amyloidosis of the Dutch-Type (HCHWA-D). In whatever form, amyloid beta peptide is a fragment of beta-amyloid precursor protein (APP) which comprises a variable number of amino acids, typically 39-43 amino acids. "Aβ(1-42)", as used herein, relates to a 42 amino acids peptide corresponding to amino acids 672 to 713 of APP and which is produced by the sequential proteolytic cleavage of the amyloid precursor protein by the β- and γ-secretases.

Amyloid beta peptides are commonly expressed as "Aβ (x-y)" wherein x represents the amino acid number of the amino terminus of the amyloid beta peptides and y represents the amino acid number of the carboxy terminus. For example, Aβ(1-40) is an amyloid beta peptide whose amino terminus begin at amino acid number 1 and carboxy terminus ends at amino acid number 40, a sequence of which is given by SEQ ID NO:1.

In the context of the present invention, "a peptide derived from the C-terminal region of Aβ(1-42)" is intended to mean peptides having from 2 to 40 amino acid residues comprising part or all of the C-terminal region of Aβ(1-42). The term also encompasses peptides comprising regions having substantial similarity to Aβ(1-42) C-terminal region, such as structural variants.

The term "substantial similarity" means that two peptide sequences, when optimally aligned, share at least 50 percent sequence identity, preferably at least 60 percent sequence identity, more preferably at least 70 percent sequence identity, more preferably at least 80 percent sequence identity, more preferably at least 90 percent sequence identity, more preferably at least 95 percent sequence identity or more (e.g., 99 percent sequence identity). Preferably, residue positions, which are not identical, differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine.

Residue positions, which are not identical, may also be composed of peptide analogs, including unnatural amino acids or derivatives of such. Analogs typically differ from naturally occurring peptides at one, two or a few positions, often by virtue of conservative substitutions.

Some analogs also include unnatural amino acids or modifications of N or C terminal amino acids at one, two or a few positions. Examples of unnatural amino acids, without limiting to, are D-amino acids, alpha, alpha-disubstituted amino acids, N-alkyl amino acids, lactic acid, 4-hydroxyproline, γ-carboxyglutamate, epsilon-N,N,N-tri methyllysine, epsilon-N-acetyllysine, O-phosphoserine, N-acetylserine, N-formylmethionine, 3-methylhistidine, 5-hydroxylysine, omega-N-methylarginine, and isoaspartic acid.

In a particular embodiment of the conjugation of the invention, the peptide derived from the C-terminal region of Aβ(1-42) is selected from Aβ(35-42) (SEQ ID NO: 2), Aβ(33-42) (SEQ ID NO: 3) y Aβ(33-40) (SEQ ID NO: 4).

"Aβ(35-42)" as used herein, relates to an 8 amino acids peptide corresponding to the last 8 amino acids of Aβ(1-42).

"Aβ(33-42)" as used herein, relates to a 10 amino acids peptide corresponding to the last 10 amino acids of Aβ(1-42).

"Aβ(33-40)" as used herein, relates to an 8 amino acids peptide corresponding to the amino acids from 33 to 40 of Aβ(1-42).

The peptides derived from the C-terminal region of Aβ(1-42), including peptide linker groups, may be synthesized by standard methods of solid or solution phase peptide chemistry. A summary of the solid phase techniques may be found in Stewart and Young (1963) Solid Phase Peptide Synthesis, W. H. Freeman Co. (San Francisco), and Meienhofer (1973) Hormonal Proteins and Peptides, Academic Press (New York). For classical solution synthesis see Schroder and Lupke, The Peptides, Vol. 1, Academic Press (New York).

In general, these methods comprise the sequential addition of one or more amino acids or suitably protected amino acids to a growing peptide chain. Normally, either the amino or carboxyl group of the first amino acid is protected by a suitable protecting group. The protected amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth. After all the desired amino acids have been linked in the proper sequence, any remaining protecting groups (and any solid support) are removed sequentially or concurrently to afford the final peptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. In a preferred embodiment, a cysteine residue is added to the N-terminus of said immunogenic peptides in order to facilitate coupling of said peptides to a carrier molecule using bifunctional reagents capable of reacting with sulfhydril groups of the cysteine.

Albumin

As mentioned above, one aspect of the present invention relates to a conjugate comprising a peptide derived from the C-terminal region of Aβ(1-42) and albumin for its use in medicine.

As used herein, "albumin" refers to the most abundant protein in blood plasma having a molecular weight of approximately between 65 and 67 kilodaltons in its monomeric form, depending on the species of origin. The term "albumin" is used interchangeably with "serum albumin" and is not meant to define the source of the albumin which forms a conjugate with the modified peptides of the invention. Thus, the term "albumin" as used herein may refer either to albumin purified from a natural source such as blood or serous fluids, or it may refer to chemically synthesized or recombinantly produced albumin. In various embodiments, albumin variants or derivatives of native albumins can be used for formation of conjugates of the invention. In some embodiments, the albumin is a mammalian albumin, or a variant or derivative thereof. Non-limiting examples of mammalian albumins that can be used include human, bovine, ovine, caprine, rabbit, feline, canine, porcine, primate, or rodent albumin. In a preferred embodiment, the mammalian albumin is human albumin.

In one embodiment, the human albumin is purified from blood or serous fluids. For example, albumin can be purified from serum or plasma samples of individuals or of laboratory animals, being the more used bovine albumin, but it can also be extracted from sera coming from other animals (chicken, pig, rabbit, etc) using any standard method such as cold ethanol fractionation by the Cohn process (Cohn E J et al., *J Am Chem Soc* 1946; 68:459-75) or by the Kistler and Nitschmann process (Kistler P and Nitschmann H S., *Vox Sang* 1962; 7:414-24) or by chromatographic purification (Bergloff J H. et al. In: Curling J M, ed. *Separation of Plasma Proteins*. Uppsala: Pharmacia, 1983; 51-8) or a combination of cold ethanol fractionation and chromatographic purification. Albumin may also be obtained from egg white (ovalbumin). A different kind of albumin, storage albumins can be extracted from the seeds of some plants (e.g. soya).

In another embodiment, the albumin is recombinant albumin. In a particular embodiment, the albumin is recombinant human albumin (referred to herein as "rHA"). In various embodiments, rHA can be produced in a mammalian or non-mammalian organism. In one embodiment, the rHA is produced in a non-mammalian organism. Examples of non-mammalian organisms that can be used for the production of rHA include, without limitation, yeast, bacteria, plants, fungi, and insects. In one embodiment, the rHA is produced in a whole plant or a whole fungus. In another embodiment, the rHA is produced in cultured plant cells, cultured fungus cells, or cultured insect cells. In another embodiment, the rHA is produced in a non-human mammal or in non-human mammalian cells. Examples of non-human mammals that can be used for the production of rHA include, without limitation, those belonging to one of the following: the family Bovidae, the family Canidae, the family Suidae, the order Rodentia, the order Lagomorpha, and the order Primates (excluding humans). In a particular embodiment, the non-human mammal that is used for the production of rHA is selected from the group consisting of a cow, a dog, a pig, a sheep, a goat, a rat, a mouse, a rabbit, a chimpanzee, and a gorilla. In another embodiment, the non-human mammalian cells used for the production of rHA are, without limitation, bovine, canine, porcine, ovine, caprine, rodent, rabbit, or non-human primate cells. The main advantage of rHA produced in a non-human organism compared with albumin purified from human blood or serous fluids is the absence of human-derived products in the manufacturing process of rHA. The use of such controlled production methods leads to a purer product with less structural heterogeneity. Previous studies have indicated that there is no significant difference between soluble rHA and human albumin purified from blood or serous fluids in terms of their biochemical characteristics, radiolabelling efficiency and biological behaviour in vitro and in vivo. See Dodsworth et al., 1996, Biotechnol. Appl. Biochem. 24: 171-176. In a particular embodiment, the albumin is the rHA designated by the trade name RECOMBUMIN® (Novozymes Inc., Nottingham, UK). RECOMBUMIN® is a recombinant human albumin that is produced in vitro using recombinant yeast technology, in which genetically modified yeast (*Saccharomyces cerevisiae*) secrete soluble rHA which is subsequently harvested, purified and formulated for use as an excipient for the manufacture of biologies or a coating for medical devices.

Alternatively, albumin, albumin variants or derivatives for use in forming a conjugate of the present invention may be obtained from a commercial source, e.g., as RECOMBUMIN® (Novozymes Inc., Nottingham, UK); PLASBUMIN® (Talecris Biotherapeutics, Research Triangle Park, N.C.); ALBAGEN®, (New Century Pharmaceuticals, Huntsville, Ala.); human albumin (Cortex-Biochem, San Leandro, Calif.), human serum albumin, ZLB Behring (King of Prussia, Pa.), or ALBREC® (Mistubishi Pharma, Japan).

In the context of the present invention, "albumin" refers to any protein with water solubility, which is moderately soluble in concentrated salt solutions, and experiences heat coagulation (protein denaturation). It has a molecular weight of about 65,000 consisting of a variable number of amino acids ranging from 609 in most species, including human albumin to 615 amino acids such as the chicken albumin. They all contain 35 cysteine residues which can be used for conjugation of the immunogenic peptide via a disulfide bond. Albumin proteins suitable for obtaining conjugates according to the present invention include, without limitation, human albumin (SEQ ID NO:5) or the mature portion thereof (amino acids 25 to 609 of SEQ ID NO:5) and bovine albumin (SEQ ID NO:6) or the mature portion thereof (amino acids 25 to 607 of SEQ ID NO:6). The albumin used in the present invention also encompasses albumin structural variants, coming from conservative amino acid substitutions as explained above for the peptide derived from Aβ(1-42) C-terminal region.

In certain embodiments, the conjugates of the invention comprise molecular variants of albumin, for example as those described in WO 2005/058958, the content of which is incorporated by references herein in its entirety. A recombinant human serum albumin variant is commercially available from New Century Pharma (Huntsville, Ala.) under the name Albagen™. Albumin used to form a conjugate according to the present invention may be obtained using methods or materials known to those of skill in the art. For instance, albumin can be obtained from a commercial source, e.g., Novozymes Inc. (Davis, Calif.; recombinant human albumin derived from *Saccharomyces cerevisiae*); Cortex-Biochem (San Leandro, Calif.: serum albumin), Talecris Biotherapeutics (Research Triangle Park, N.C.; →erum albumin). ZLB Behring (King of Prussia. Pa.), or New Century Pharmaceuticals ille, Ala.: recombinant human albumin derived from *Pichia pastupsilonris*).

Variants of albumin may include natural variants resulting from the polymorphism of albumin in the human population. More than 30 apparently different genetic variants of human serum albumin have been identified by electrophoretic analysis under various conditions. See e.g., Weitkamp et al, Ann. Hum. Genet., 36(4):381-92 (1973); Weitkamp, Isr. J. Med. ScL, 9(9):1238-48 (1973); Fine et al, Biomedicine, 25(8): 291-4 (1976); Fine et al, Rev. Fr. Transfus. immunohematoL, 25(2): 149-63. (1982); Rochu et al, Rev. Fr. Transfus. Immunohematol. 31(5):725-33 (1988); Arai et al, Proc. Natl. Acad. Sd. U.S.A 86(2): 434-8 (1989), the contents of which are hereby incorporated by reference in their entireties. In a specific embodiment, the invention provides conjugates formed with molecular variants of albumin.

In some embodiments, conjugates of the invention comprise derivatives of albumin which share substantial homology with albumin. For instance, conjugates may be formed with an albumin homologue having an amino acid sequence at least 75 percent, at least 80 percent, at least 85 percent, more typically at least 90 percent, and most typically at least 95 percent, the same as that of albumin. In certain embodiments, the albumin homologue comprises a free cysteine.

In some embodiments, conjugates of the invention comprise structural derivatives of albumin. Structural derivatives of albumin may include proteins or peptides which possess an albumin-type activity, for example, a functional fragment of albumin In some embodiments, the derivative is an antigenic determinant of albumin, i e, a portion of a polypeptide that can be recognized by an anti-albumin antibody In some embodiments, the recombinant albumin may be any protein with a high plasma half-life which may be obtained by modification of a gene encoding human serum albumin. By way of example and not limitation, the recombinant albumin may contain insertions or deletions m the trace metal binding region of albumin, such that binding of trace metals, e g, nickel and/or copper is reduced or eliminated, as described in U.S. Pat. No. 6,787,636, the content of which is incorporated by reference in its entirety. Reduced trace metal binding by albumin may be advantageous for reducing the likelihood of an allergic reaction to the trace metal in the subject being treated with the albumin composition.

In certain embodiments, albumin derivatives include any macromolecule with a high plasma half-life obtained by in vitro modification of the albumin protein. In some embodiments, the albumin is modified with fatty acids. In some embodiments, the albumin is modified with metal ions. In some embodiments, the albumin is modified with small molecules having high affinity to albumin. In some embodiments, the albumin is modified with sugars, including but not limited to, glucose, lactose, mannose and galactose.

Structural derivatives of albumin may be generated using any method known to those of skill in the art, including but not limited to, oligonucleotide-mediated (site-directed) mutagenesis, alanine scanning, and polymerase chain reaction (PCR) mutagenesis. Site-directed mutagenesis (see Cotter, Biochem J 237 1-7 (1986), Zoller and Smith, Methods Enzymol 154 329-50 (1987)), cassette mutagenesis, restriction selection mutagenesis (Wells et alpha1, Gene 34 315-323 (1985)) or other known techniques can be performed on cloned albumin-encoding DNA to produce albumin variant DNA or sequences which encode structural depivatives of albumin (Ausubel et alpha1, Current Protocols In Molecular Biology, John Wiley and Sons, New York (current edition), Sambrook et al, Molecular Cloning, A Laboratory Manual, 3d ed, Cold Spring Harbor Laboratory Press, Cold Spring Harbor, N.Y. (2001), the contents of which are hereby incorporated by reference in their entireties In certain embodiments, albumin derivatives include any macromolecule by in vitro modification of the albumin protein with a plasma half-life higher than native albumin In some embodiments, the albumin is modified with one or more fatty acids In some embodiments, the albumin is modified with one or more metal ions In some embodiments, the albumin is modified with one or more small molecules having high affinity to albumin In some embodiments, the albumin is modified with one or more sugars, including but not limited to, glucose, lactose, mannose, and galactose.

Preparations of human serum albumin, whether serum derived or recombinantly produced, may comprise a heterogeneous mixture of non-mercaptalbumin, i.e., "capped" albumin, and mercaptalbumin, i.e., "uncapped" albumin. The human albumin polypeptide contains 35 cysteinyl residues, of which 34 form 17 stabilizing disulfide bridges. While the cysteine residue at position 34 of mercaptalbumin comprises a free SH group, the same residue in non-mercaptalbumin comprises a mixed disulfide with, for example, cysteine or glutathione, or has undergone oxidation by metal ions or other adducts, thus rendering the thiol group less reactive or unavailable. Typically, enrichment for mercaptalbumin is achieved contacting the recombinant albumin with any agent capable of converting oxidized albumin-Cys34 to reduced albumin-Cys34 such as dithiothreitol (DTT), thioglycolic acid (TGA) or beta-mercaptoethanol (BME).

In certain embodiments of the invention, the recombinant albumin may be deglycated prior to proceeding with the conjugation reaction. It is believed that deglycation of albumin, particularly recombinant albumin produced in yeast, may yield albumin having advantageous tolerability and stability with respect to conjugates formed therewith. Generally, deglycation of albumin may be carried out using any technique and under any conditions known to those of skill in the art to be useful for the reduction of non-enzymatically glycated proteins such as those described by Miksik et al (J. Chromatogr. B. Biomed. Sci. Appl., 1997, 699:311-345). Alternatively, albumin may be deglycated using enzymatic methods. For instance, deglycation can be carried out using endoglycosidase H, or with a mixture of different endoglycosidases.

In another embodiment, the recombinant albumin may be further processed for favorable specificity of conjugation, i.e. to reduce the likelihood of formation of non-Cys34 conjugates. For instance, the recombinant albumin may be contacted with agents which chemically block residues at which covalent adduct formation is known to occur on human serum albumin. Any agent known in the art capable of blocking reactive sites on albumin other than Cys34 may be used. In some embodiments, the agent blocks a lysine residue. Albumin contains a variable number of lysine residues (for instance, 60 in the human albumin and 61 in the bovine albumin), 25-30 of which are located on the surface of albumin and may be accessible for conjugation. Accordingly, in some embodiments, the agent blocks any lysine residue of albumin known to those of skill in the art as having the potential to form covalent adducts, such as Lys71, Lys199, Lys351, Lys525, Lys541 of albumin.

Linker Region

The peptide derived from the C-terminal region of Abeta (1-42) and albumin may be directly attached or, alternatively, may be connected via one or more linking groups (hereinafter also referred to as intervening molecules or spacer moiety).

In a particular embodiment of the conjugation of the invention, if the at least one immunogenic peptide and the albumin are connected by a linker region; said linker region contains attached thereto not more than one immunogenic peptide.

In another particular embodiment of the conjugation of the invention, the linker region connecting the at least one immunogenic peptide and the albumin comprise a cysteine, more preferably the cysteine is located at the N-terminus of the immunogenic peptide.

In certain embodiments, the linking group is a biocompatible polymer, e.g., a peptide or an alkyl or an alkoxy containing polymer. In a specific embodiment, the linking group is a peptide having a labile chemical bond which is cleavable by an enzyme or which is cleaved under specific chemical conditions, e.g., acidic conditions. In one embodiment, the modified peptide comprises a reactive group covalently attached to the peptide through one or more linking groups. In certain embodiments, the linking group includes one or more reactive groups, typically one linking group. In certain embodiments, the linking group has a length of 1 to 100 atoms. As described herein, the length of a linking group is expressed by the number of atoms in the shortest chain of atoms between the groups linked by the linking group. In certain embodiments, the linking group has from 1 to 100 atoms, from 1 to 80 atoms, from 1 to 60 atoms, from 1 to 50 atoms, from 1 to 40 atoms, from 1 to 30 atoms, from 1 to 20 atoms, from 10 to 20 atoms or from 5 to 15 atoms. Where more than one linking group is present, the linking groups may be the same or different linking groups. The linking group can be attached to the peptide derived from the C-terminal region of Abeta(1-42) by any method or technique known to those of skill in the art. Exemplary methods or techniques are described in U.S. Pat. No. 6,849,714, the contents of which are hereby incorporated by reference in its entirety.

Linking groups may comprise one or more alkyl groups such as methyl, ethyl, propyl, butyl, etc. groups, alkoxy groups, alkenyl groups, alkynyl groups or amino group substituted by alkyl groups, cycloalkyl groups, polycyclic groups, aryl groups, polyaryl groups, substituted aryl groups, heterocyclic groups, and substituted heterocyclic groups.

In certain embodiments, the linking group may be selected from linking groups including an amino group and a carboxy group including, but not limited to, AEA, AEEA and OA. In certain embodiments, the linking group may be a polymer of AEA having a length of 1 to 100 atoms. In certain embodiments, the linking group may be an AEEA polymer having a length of 1 to 100 atoms. In certain embodiments, the linking group may be an OA polymer having a length of 1 to 100 atoms. Illustrative examples of linking groups include monomers, dimers, trimers, tetramers, pentamers, sixmers, septamers, octamers, nonamer, decamer, undecamers, dodecamers of glycine, lysine, glutamate, isoleucine, or arginine residues, AEA, AEEA or OA (e.g., an OA dimer (-OA-OA-) or an OA trimer (-OA-OA-OA-), or any combination thereof (e.g., any combination of $Gly_n$, $LyS_n$, OA, AEA, or AEEA, wherein n=1, 2, 3, 4, 5, 6, 7, 8, 9, 10, 11, or 12). In some embodiments, the linking group has a single lysine. The single lysine can be modified to be linked to a reactive group directly or via one or more linking groups. For example, the K group may be linked to the reactive group or one or more additional linkers through, for example, the epsilon amino group of the side chain. Examples of such linkers including a single lysine have, for example, the sequence of (monomer)$_a$K(monomer)$_b$, K(monomer)c, and (monomer)$_d$K, where a, b, c and d are each an integer greater than or equal to one, for example, one, two, three, four, five, six, seven, eight, nine, ten, eleven, twelve or more. In some examples, a and b may be the same, whereas in other examples a and b are not the same. For example, a may be three and b may be four to provide a linking group having the following sequence: (OA)$_n$K(OA)$_n$, (OA)$_n$K(AEA)$_n$, (G)$_n$K(OA)$_n$, (OA)$_n$K(G)$_n$, wherein n=1, 2, 3, 4, 5, 6, 7, 8, 9, 10, 11, or 12. In the case where the reactive group is located on the linker between the two TMPs, the total length between the two TMPs will not typically exceed 100 atoms. The attachments to the linker group are not considered to be part of the linker between the two TMPs.

The linking group can include any combinations of the aforesaid biocompatible polymers. For example, a polyglycine linker can be combined with one or more monomers of AEA, AEEA or OA in any configuration. In one embodiment, the polyglycine linker is attached to one or more monomers of AEA, AEEA or OA at either the N- or the C-terminal end of the first or last glycine residue in the polyglycine linker. Alternatively one or more monomers of AEA, AEEA or OA are inserted in between glycine residues in the polyglycine linker. In particular embodiments, the reactive group (for example, MPA, GMBA, NHS, sulfo-NHS, MBS or GMBS), is attached to the peptide through one or more linking groups, including, for example, a polyglycine linker, a polyglycine-lysine linker, AEEA, AEA, or OA, or any combination thereof. In certain embodiments in which the reactive group is attached to the peptide through more than one linking group, each linking group can be independently selected from the group consisting typically of, polyglycine, polylysine, AEA, AEEA, and OA. In embodiments, the number of linking groups (e.g., monomeric polymer units) is from 1 to 2, 1 to 3, 1 to 4, 1 to 5, 1 to 6, 1 to 7, 1 to 8, 1 to 9, 1 to 10, 1 to 11, 1 to 12. Where there is more than one linking group, the linking groups can be the same or different linking groups. For example, any combination of one of polyglycine, polylysine, AEA, AEEA, and/or OA can be used in any order. In one embodiment, the reactive group, typically MPA, is attached to the peptide via 1, 2, 3, 4, 5, 6, 7, 8, 9, 10, 11, or 12 polyglycine, polylysine, AEA, AEEA or OA linking groups which are arranged in tandem. In another embodiment, the reactive group, typically MPA, is attached to the peptide via 1, 2, 3, 4, 5, 6, 7, 8, 9, 10, 11, or 12 polyglycine, polylysine, AEA, AEEA or OA linking groups which are arranged in a branched configuration.

In another embodiment, the linking group is a peptide moiety which is capable of acting as hinge regions between the peptide derived from Aβ(1-42) C-terminal region and the albumin, allowing them to move independently from one another while they maintain their own individual three-dimensional shape. In this sense, a preferred non-natural intermediate amino acid sequence according to the invention would be a hinge region characterized by a structural ductility allowing this movement, or a non-natural flexible linker. The flexible linker can be a flexible linker peptide with a length of 20 amino acids or less. In a more preferred embodiment, the linker peptide comprises 2 amino acids or more selected from the group consisting of glycine, serine, alanine and threonine.

In a preferred embodiment of the invention, said flexible linker is a polyglycine linker, but are not limited to, polyglycine, polyglutamate, polyisoleucine, polyarginine or other suitable linking groups including two or more amino acids. In some examples, the amino acid linking groups can include at least two, three, four, five, six, seven, eight, nine, ten, eleven or twelve amino acid residues, for example, glycine or lysine residues. A polyglycine linker can include one or more different residues (e.g., lysine residues) inserted in any configuration, e.g., near the N- or C-terminal end, or in the middle of a stretch of glycine residues. In other embodiments, a polyglycine linker is combined with one or more monomers of AEA, AEEA or OA in any configuration. In one embodiment, the polyglycine linker is attached to one or more monomers of AEA, AEEA or OA at either the N- or the C-terminal end of the first or last glycine residue in the polyglycine linker. Alternatively one or more monomers of AEA, AEEA or OA are inserted in between glycine residues in the polyglycine linker. In examples, where a polyglycine is used as a linker, the polyglycine may include a single lysine to provide a free epsilon amino group capable of reacting with another linker or with a protein. Examples of such a polyglycine that includes an amino acid, e.g., a single lysine, have, for example, an amino acid sequence of (G)$_a$K(G)$_b$, K(G)c, and (G)$_d$K. where a, b, c and d are each an integer greater than or equal to one, for example, one, two, three, four, five, six, seven, eight, nine, ten, eleven, twelve or more. In some examples, a and b may be the same, whereas in other examples a and b are not the same. For example, a may be three and b may be four. In some examples, the single lysine within the polyglycine linker may itself be linked to additional moieties, e.g., a linking group, a reactive group or a residue of a reactive group. For example, the lysine residue may be linked to one or more additional linkers through, for example, the epsilon amino group of the side chain.

Possible examples of linker/spacer sequences include SGGTSGSTSGTGST (SEQ ID NO:7), AGSSTGSSTGPG-STT (SEQ ID NO:8) or GGSGGAP (SEQ ID NO:9) and GGGKGGGG (SEQ ID NO: 10). These sequences have been used for binding designed coiled helixes to other protein domains (Muller, K. M., Arndt, K. M. and Alber, T., Meth. Enzymology, 2000, 328: 261-281). Said linker preferably comprises or consists of the amino acid sequence GGGVEGGG (SEQ ID NO: 11).

The effect of the linker region is providing space between the peptide derived from the C-terminal region of Aβ(1-42) and the albumin. It is thus ensured that the secondary structure of the peptide derived from Aβ(1-42) C-terminal region is not affected by the presence of albumin and vice versa. The spacer preferably has a peptide nature. The linker peptide preferably comprises at least two amino acids, at least three amino acids, at least five amino acids, at least ten amino acids, at least 15 amino acids, at least 20 amino acids, at least 30 amino acids, at least 40 amino acids, at least 50 amino acids, at least 60 amino acids, at least 70 amino acids, at least 80 amino acids, at least 90 amino acids or approximately 100 amino acids.

Additionally, the linker can be bound to components flanking the peptide derived from the C-terminal region of Aβ(1-42) and the albumin by means of covalent bonds and preferably the spacer is essentially non-immunogenic and/or does not comprise any cysteine residue. In a similar manner, the three-dimensional structure of the spacer is preferably linear or substantially linear.

The linker can include residues 53-56 of tetranectin, forming a β sheet in tetranectin, and residues 57-59 forming a turn in the tetranectin (Nielsen, B. B. et al., FEBS Lett. 412:

388-396, 1997). The sequence of the segment is GTKVHMK (SEQ ID NO:12). This linker has the advantage that when it is present in native tetranectin, it binds the trimerization domain with the CRD domain, and therefore it is suitable for connecting the trimerization domain to another domain in general. Furthermore, the resulting construct is not expected to be more immunogenic than the construct without a linker.

Alternatively, a subsequence from the connecting strand 3 from human fibronectin can be chosen as a linker, corresponding to amino acids 1992-2102 (SWISSPROT numbering, entry P02751). The subsequence PGTSGQQPSVGQQ (SEQ ID NO: 13) corresponding to amino acids number 2037-2049 is preferably used, and within that subsequence fragment GTSGQ (SEQ ID NO: 14) corresponding to amino acids 2038-2042 is more preferable. This construct has the advantage that it not very prone to proteolytic cleavage and is not very immunogenic because fibronectin is present at high concentrations in plasma.

Alternatively, a suitable peptide linker can be based on the 10 amino acid residue sequence of the upper hinge region of murine IgG3. This peptide (PKPSTPPGSS, SEQ ID NO: 15) has been used to produce antibodies dimerized by means of a coiled helix (Pack P. and Pluckthun, A., 1992, Biochemistry 31:1579-1584) and can be useful as a spacer peptide according to the present invention. A corresponding sequence of the upper hinge region of human IgG3 can be even more preferable. Human IgG3 sequences are not expected to be immunogenic in human beings. In a preferred embodiment, the linker peptide is selected from the group of the peptide of sequence APAETKAEPMT (SEQ ID NO: 16) and of the peptide of sequence GAP.

In a particular embodiment, the linker region does not comprise the following groups:

In a particular embodiment, the conjugate of the invention does not have the following structure:

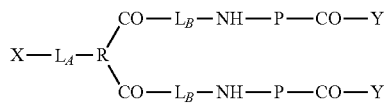

wherein
R represents

X represents a hydrogen or a peptidic group, and
$L_A$ is optionally present and is an amino acid or a peptide containing at least 2 amino acid residues,
$L_B$ is optionally present and is an amino acid or a peptide containing at least 2 amino acid residues,
P is a peptide selected from full length or fragments of amyloid proteins or proteins with substantial similarity to an amyloid protein,
Y is OH or $NH_2$,
and pharmaceutically acceptable salts thereof.

Conjugation of Peptide Derived from the C-terminal Region of Aβ(1-42) and Albumin Once a sufficient amount of peptide derived from the C-terminal region of Aβ(1-42) and of albumin is available, a conjugate of the invention is formed by contacting both components under conditions suitable for the formation of a covalent complex between them.

Irrespective of whether the immunogenic peptide and the albumin are directly linked of connected by a linking group, the invention contemplates both the possibility of the peptide being connected through its N-terminus (C-terminally presented) or being connected to the albumin molecule through its C-terminus (N-terminally presented). In a preferred embodiment, the immunogenic peptide is C-terminally presented in the albumin molecule. The term "C-terminally presented", as used herein, refers to peptides which are linked to the carrier protein (albumin) through its N-terminal region so that the C-terminus remains available for recognition by the immune system.

When the peptide and the albumin molecule are connected via a linker, this has been usually achieved by the use of homobifunctional reagents which are capable of reacting with the free α-amino group at the N-terminus of the peptide and with primary amino groups in the albumin molecule, either from lysine groups or the free α-amino group at the N-terminus. Suitable homobifunctional reagents for connecting primary amino groups of the immunogenic peptide and albumin include, without limitation, dialdehydes such as glutaraldehyde, glyoxal, succinaldehyde, ethyl succinaldehyde, 2-methylglutaraldehyde, 3-methylglutaraldehyde, adipaldehyde, and the like.

The albumin is contacted with a peptide derived from the C-terminal region of Aβ(1-42) in a solution comprising a final molar ratio of peptide to albumin of about 0.1:1 to about 10,000:1. In some embodiments, the final molar ratio is about 7500:1, 5000:1, about 2500:1, about 1000:1, about 750:1, about 500:1, about 250:1, about 100:1, about 75:1, about 50:1, about 25:1, about 10:1, about 7.5:1, about 5:1, about 2.5:1, or about 1:1. In some embodiments, the final molar ratio is between about 0.1:1 to 1:1. In some embodiments, the final molar ratio is about 0.1:1, 0.2:1, 0.3:1, 0.4:1, 0.5:1, 0.6:1, 0.7:1, 0.8:1, 0.9:1.

Coupling of the first and second component of the conjugate takes place by means of a reactive group which is coupled to any site of the peptide derived from the C-terminal domain of Aβ(1-42). The reactive group is chosen for its ability to form a stable covalent bond with albumin, for example, by reacting with one or more amino groups, hydroxyl groups, or thiol groups on albumin. Preferably, a reactive group reacts with only one amino group, hydroxyl group, or thiol group on albumin. Accordingly, the reactive group can be linked to any site of the peptide or a linking group deemed suitable according to one of skill in the art. In certain embodiments, the reactive group is linked to the backbone of the peptide or derivative. In certain embodiments, the reactive group is linked to the N-terminus, e.g., the N-terminal amine, of the peptide or derivative. In certain embodiments, the reactive group is linked to the C-terminus, e.g., the C-terminal carboxyl, of the peptide or derivative. In certain embodiments, the reactive group is linked to a side chain of the peptide or derivative, e.g., a side chain hydroxyl, thiol, amino or carboxyl, of the peptide or derivative. In specific embodiments, the reactive group is linked to the epsilon amino group of a lysine side chain of the peptide or derivative. In specific embodiments, the reactive group is linked to a cysteine residue found within the N-terminus or the C-terminus of the peptide.

To form covalent bonds with the functional group on a protein, one may use as a chemical reactive group a wide variety of active carboxyl groups, particularly esters. The carboxyl groups are usually converted into reactive intermediates such as N-hydroxy succinimide (NHS) or maleimide that are susceptible to attack by amines, thiols and hydroxyl functionalities on the protein. Introduction of NHS and maleimide reactive groups on the peptide can be performed by the use of bifunctionnal linking agents such as maleimide-benzoyl-succinimide (MBS), gamma-maleimido-butyryloxy succinimide ester (GMBS), dithiobis-N-succinimidyl propionate (DTSP), N-succinimidyl 3-(2-pyridyldithio) (SPDP), succinimidyl trans-4-(maleimidylmethyl)-cyclohexane-1-carboxylate (SMCC), succinimidy 1 acetylthioacetate (SATA), benzophenone 4-maleimide. Lambda-((2-pyridyldifhio)ethyl)-4-azidosalicylamide (PEAS; AET). Such bifunctionnal linkers will activate either carboxy or amino groups on the peptide based on the choice of protecting groups.

Alternatively the addition of maleimide to the peptide can be performed through the use of coupling agents such as N,N, dicyclohexylcarbodiimide (DCC). 1-ethyl-3-{3-dimethy laminopropyl) carbodiimide, hydrochloride (EDAC) and the likes to activate derivatives like maleimidopropionic acid. [2-[2-[2-maleimidopropionamido(ethoxy)ethoxy]acetic acid, and subsequently react with an amine on the peptide. Similar agents like DCC and EDAC could also be used to add derivatives like maleimidoalkyl amines to carboxy moieties on the peptide.

Primary amines are the principal targets for NHS esters. Accessible epsilon-amine groups present on the N-termini of proteins react with NHS esters. However, epsilon-amino groups on a protein may not be desirable or available for the NHS coupling. While five amino acids have nitrogen in their side chains, only the epsilon-amine of lysine reacts significantly with NHS esters. An amide bond can form when the NHS ester conjugation reaction reacts with primary amines releasing N-hydroxysuccinimide. These succinimidyl-containing reactive groups are herein referred to as succinimidyl groups.

In particular embodiments, the functional group on albumin is the single free thiol group located at amino acid residue 34 (Cys34) and the chemically reactive group is a maleimido-containing group such as MPA. MPA stands for maleimido propionic acid or maleimidopropionate. Such maleimido-containing groups are referred to herein as maleimido groups.

In some embodiments, conjugates formed by the processes described herein comprise albumin covalently linked to a succinimidyl or maleimido group on a therapeutic peptide. In some embodiments, an albumin amino, hydroxyl or thiol group is covalently linked to a succinimidyl or maleimido group on the therapeutic peptide. In some embodiments, albumin cysteine 34 thiol is covalently linked to a [2-[2-[2-maleimidopropionamido(ethoxy)ethoxy]acetamide linker on the epsilon amino of a lysine of the therapeutic peptide.

In a specific embodiment, the reactive group is a single MPA reactive group attached to the peptide, optionally through a linking group, at a single defined amino acid and the MPA is covalently attached to albumin at a single amino acid residue of albumin, preferably cysteine 34. In a preferred embodiment, the albumin is recombinant human albumin.

In certain embodiments, the reactive group can be attached to any residue of the therapeutic peptide suitable for attachment of such a reactive group. The residue can be a terminal or internal residue of the peptide. In certain embodiments, the reactive group can be attached to the carboxy-terminus or amino-terminus of the peptide. In advantageous embodiments, the reactive group is attached to a single site of the peptide. This can be achieved using protecting groups known to those of skill in the art. In certain embodiments, a derivative of the therapeutic peptide can comprise a residue incorporated for attachment of the reactive group. Useful residues for attachment include, but are not limited to, cysteine, lysine, aspartate and glutamate residues. The residue can be incorporated internally or at a terminus of the peptide, for example on the N-terminal amino-acid residue via the free alpha-amino end. In certain embodiments, the reactive group is attached to an internal lysine residue. In certain embodiments, the reactive group is attached to a terminal lysine residue. In certain embodiments, the reactive group is attached to an amino-terminal lysine residue. In certain embodiments, the reactive group is attached to a carboxy-terminal lysine residue, for instance, a lysine residue at the carboxy-terminus of the therapeutic peptide.

In other embodiments, an activated disulfide bond group may be coupled to a therapeutic peptide cysteine or cysteine analog through a method for the preferential formation of intermolecular disulfide bonds based on a selective thiol activation scheme. Methods based on the selective activation of one thiol with an activating group followed by a reaction with a second free thiol to form asymmetric disulfide bonds selectively between proteins or peptides have been described to alleviate the problem of reduced yields due to symmetric disulfide bond formation. See D. Lambdandreu et al, "Methods in Molecular Biology" (M. W. Pennington and B. M. Dunn, eds.). Vol. 35, p. 91. Humana Press. Totowa. N.J., (1994). Preferably, such activating groups are those based on the pyridine-sulfenyl group (M. S. Bernatowicz el id., Int. J. Pept. Protein Res. 28: 107 (1986)). Preferably. 2,2'-dithiodipyridine (DTDP) (Carlsson et al., Diupsilonchem. J. 173: 723 (1978); L. H. Kondejewski et al., Bioconjugate Chem. 5:602(1994) or 2.2'-dithiobis(5-Nitropyridine) (NPYS) (J. Org. Chem. 56: 6477 (1991)) or N-succinimidyl 3-(2-pyridyldithio) (SPDP) are employed. In addition, 5,5'-difhiobis (2-nitrobenzoic acid) (Ellman's reagent) or 6,6'-dithiodinicotinic acid may be used as activating groups.

In accordance with these methods, a disulfide bond activating group is first reacted with a therapeutic peptide containing a cysteine or cysteine analog under conditions of excess activating group. These conditions highly favor the formation of the therapeutic compound containing a therapeutic peptide coupled with an activated disulfide group, with essentially no production of disulfide-bonded peptide homodimers. Following the coupling reaction, the resulting peptide compound is purified, such as by reversed phase-HPLC. A reaction with a second free thiol occurs when the peptide compound is reacted with albumin, to form a conjugate between the therapeutic compound and serum albumin.

A therapeutic peptide cysteine or cysteine analog is converted to having an S— sulfonate through a sulfitolysis reaction scheme. In this scheme, a therapeutic peptide is first synthesized either synthetically or recombinantly. A sulfitolysis reaction is then used to attach a S-sulfonate to the therapeutic peptide through its cysteine or cysteine analog thiol, following the sulfitolysis reaction, the therapeutic peptide compound is purified, such as by gradient column chromatography. The S-sulfonate compound is then used to form a conjugate between the therapeutic peptide compound and a blood component, preferably serum albumin.

The manner of modifying therapeutic peptides with a reactive group for conjugation to albumin will vary widely, depending upon the nature of the various elements comprising the therapeutic peptide. The synthetic procedures will be selected so as to be simple, provide for high yields, and allow for a highly purified product. Normally, the chemically reactive group will be created at the last stage of peptide synthesis, for example, with a carboxyl group, esterification to form an active ester. Specific methods for the production of modified insulinotropic peptides are described in U.S. Pat. Nos. 6,329, 336, 6,849,714 or 6,887,849.

The conjugation of the first and second components of the conjugate of the invention can be carried out in different ways. One possibility is the direct conjugation of a functional group to the therapeutically active component in a position which does not interfere with the activity of said component. As understood in the present invention, functional groups relates to a group of specific atoms in a molecule which are responsible for a characteristic chemical reaction of said molecule. Examples of functional groups include, but are not limited to hydroxy, aldehyde, alkyl, alkenyl, alkynyl, amide, carboxamide, primary, secondary, tertiary and quaternary amines, aminoxy, azide, azo (diimide), benzyl, carbonate, ester, ether, glyoxylyl, haloalkyl, haloformyl, imine, imide, ketone, maleimide, isocyanide, isocyanate, carbonyl, nitrate, nitrite, nitro, nitroso, peroxide, phenyl, phosphine, phosphate, phosphono, pyridyl, sulfide, sulfonyl, sulfonyl, thioester, thiol and oxidized 3,4-dihydroxyphenylalanine (DOPA) groups.

Another possibility is to conjugate the first and second components by means of the use of homo- or heterobifunctional groups. The bifunctional group can be conjugated first to the peptide derived from the C-terminal region of Aβ(1-42) and then conjugated to the albumin or, alternatively, it is possible to conjugate the bifunctional group to albumin and then, conjugate it to the peptide derived from the C-terminal region of Aβ(1-42). Illustrative examples of these types of conjugates include the conjugates known as ketone-oxime (described in US20050255042) in which the first component of the conjugate comprises an aminoxy group which is bound to a ketone group present in a heterobifunctional group which is in turn bound to an amino group in the second component of the conjugate.

In other embodiment, the agent which is used to conjugate the first and second components of the conjugate of the invention can be photolytically, chemically, thermally or enzymatically processed. It is particularly interesting to use linking agents which can be hydrolyzed by enzymes which are in the cell target, so that the therapeutically active compound is only released in the inside of the cell. Examples of types linking agents which can be intracellularly processed have been described in WO04054622, WO06107617, WO07046893 and WO07112193.

The components of the conjugate of the invention can be chemically modified with the proviso that the secondary structure and functionality of both components remain unaltered. Methods for chemically modifying a polypeptide chain are widely known for a person skilled in the art and include methods based on the conjugation through the thiol groups present in the cysteine moieties, methods based on the conjugation through the primary amino groups present in lysine moieties (U.S. Pat. No. 6,809,186), methods based on the conjugation through the N- and C-terminal moieties. Reagents suitable for modifying polypeptides to allow their coupling to other compounds include: glutaraldehyde (it allows binding compounds to the N-terminal end of polypeptides), carbodiimide (it allows binding the compound to the C-terminal end of a polypeptide), succinimide esters (for example MBS, SMCC) which allow activating the N-terminal end and cysteine moieties, benzidine (BDB), which allows activating tyrosine moieties, periodate, which allows activating carbohydrate moieties in the proteins which are glycosylated.

In a particular embodiment, the peptide derived from Aβ(1-42) C-terminal region further comprises an additional N-terminal Cys.

In another embodiment, a modified peptide comprising a serum protein is prepared in vitro (ex vivo) by covalently attaching the modified peptide to the serum protein in vitro such that a residue of the reactive group of the peptide forms a covalent bond with the serum protein. In one embodiment, the serum protein is autologous to the subject. In a specific embodiment, the serum protein is isolated from the subject. In certain embodiments, the isolated serum protein from the subject is purified from other proteins present in the blood and/or from blood cells before it is covalently attached to the modified peptide. In accordance with this embodiment, the resulting conjugate is administered to the subject from which the serum protein was isolated, or to an autologous subject. In another embodiment, the serum protein is a recombinant serum protein. Typically, the serum protein is recombinant albumin; most typically the serum protein is recombinant human albumin. In a preferred embodiment, a conjugate of the invention is formed by contacting a modified peptide comprising a maleimido group with a thiol-containing serum protein, typically albumin, under conditions comprising a pH of between 6.5 and 7.4, thereby typically forming a stable thioether linkage which cannot be cleaved under physiological conditions. In certain preferred embodiments, the serum protein is recombinant human albumin or recombinant bovine albumin)

In one embodiment, the modified peptide is amidated at its C-terminal end. In another embodiment, the modified peptide is not amidated at its C-terminal end. A modified peptide, conjugate or compound of the invention can also comprise such an amidated peptide. In one embodiment, the modified peptide is acylated at its N-terminal end. In another embodiment, the modified peptide is not acylated at its N-terminal end. A modified peptide, conjugate, compound of the invention can also comprise such an acylated peptide.

Coupling of the immunogenic peptide to albumin by means of a cysteine residue at the N-terminus of the peptide allows the coupling to a single albumin molecule of as many peptide molecules as cysteine residues are found in the albumin molecule. For instance, bovine serum albumin (BSA) contains 35 cysteine residues which can be occupied by as many as 35 N-terminally Cys-modified peptides so as to obtain a conjugate having at least 1, 2, 3, 4, 5, 6, 7, 8, 9 10, 11, 12, 13, 14, 15, 16, 17, 18, 19, 20, 21, 22, 23, 24, 25, 26, 27, 28, 29, 30, 31, 32, 33, 34 or 35 peptide molecules.

Alternatively, the coupling of the immunogenic peptide to albumin is carried out using an homobifunctional reagent capable of reacting with primary amino groups, the conjugate can comprise as many peptide molecules as lysine residues are found in the albumin molecule. For instance, bovine serum albumin (BSA) contains 58 lysine residues which can be occupied by as many as 58 immunogenic peptides so as to obtain a conjugate having at least 1, 2, 3, 4, 5, 6, 7, 8, 9 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57 or 58 peptide molecules.

Compositions of the Invention for Use in Medicine

The conjugates of the invention are capable of inducing an immune response in a subject leading to an increase in the amount of antibodies specific towards Aβ(1-42) and of reducing the amyloid load in serum. However, as it is known by the skilled person, the immune response can be increased using adjuvants in order to augment the antigenicity of the conjugate. Thus, in another aspect, the invention provides a composition comprising a conjugate of the invention and an adjuvant for use in medicine.

The term "adjuvant", as used herein, refers to an immunomodulating substance capable of being combined with the conjugate of the invention to enhance, improve or otherwise modulate an immune response in a subject without deleterious effect on the subject.

Adjuvants exert their immunomodulatory properties through several mechanisms such as lymphoid cells recruitment and cytokine induction. Cytokine adjuvants include, without limitation, granulocyte-macrophage colony-stimulating factor, interleukin-12, GM-CSF, synthetic muramyl dipeptide analog or monophosphoryl lipid A. Further examples of adjuvants are selected from the group comprising complete Freunds adjuvant, incomplete Freunds adjuvant, QS21, aluminium hydroxide gel, MF59, calcium phosphate, liposyn, saponin, squalene, L121, emulsigen monophosphyryl lipid A (MPL), polysorbate 80, cholera toxin (CT), LTK and LTK63. Preferably, the adjuvants are such, which are approved for administration to humans, such as aluminium hydroxide gel, calcium phosphate and MF59.

In a more particular embodiment, the adjuvant is of a type that stimulates a Th2 type of immune response, such as, e.g, aluminium hydroxide gel and CT. By inducing a Th2 type response, anti-inflammatory cytokine production such as IL-4, Il-10 and TGF-beta, as well as the production of $IgG_1$ and $IgG_{2b}$ antibody classes, are favoured. Preferred adjuvants for use in eliciting a predominantly TH2-type response include, for example, phosphopolymer (Guy et al. 1998, Vaccine 16:850-856) and alum (e.g., aluminium hydroxide, aluminium phosphate).

The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt.

A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{3+}$ at pH 7.4 have been reported for aluminium hydroxide adjuvants.

Aluminium phosphate adjuvants generally have a $PO_4/Al$ molar ratio between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 µm (e.g. about 5-10 µm) after any antigen adsorption. Adsorptive capacities of between 0.7-1.5 mg protein per mg $Al^{3+}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7. Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate. In this case there may be more aluminium phosphate than hydroxide e.g. a weight ratio of at least 2:1 e.g. >5:1, >6:1. >7:1, >8:1, >9:1, efc.

The concentration of $Al^{4+}$ in a composition for administration to a patient is preferably less than 10 mg/ml e.g. <5 mg/ml, <4 mg/ml, <3 mg/ml, <2 mg/ml, <1 mg/ml, etc. A preferred range is between 0.3 and 1 mg/ml. A maximum of 0.85 mg/dose is preferred.

On the other hand, the adjuvant is of a type that stimulates a Th1 type of immune response. As used herein, the term type 1 adjuvant or Th1 adjuvant is intended to define an adjuvant which stimulates a Th1 (type 1) response (or a response which is polarized or skewed towards a type 1 response, with a relatively weak Th2 (type 2) response). Th1 immune responses (characterized by production of gamma interferon (IFN-γ) and associated with protective immunity to viruses and intracellular bacteria) can be desirable and therefore, in another particular embodiment, the adjuvant is of a type that stimulates a Th1 type of immune response. Preferred adjuvants for use in eliciting a predominantly Th1-type response may be selected from the group consisting of complete Freund's adjuvant, monophosphoryl lipid A, 3-de-O-acylated monophosphoryl lipid A (3D-MPL), aluminum salt, CpG-containing oligonucleotides, immunostimulatory DNA sequences, saponin, Montanide ISA 720 (Seppic, France), SAF, ISCOMS (CSL), MF-59 (Chiron), SBAS-3, SB. Other preferred Th1 adjuvants include SAF (Chiron, Calif., United States), the SBAS series of adjuvants (e.g., SBAS-2 or SBAS-4, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in U.S. Pat. Nos. 6,113,918 and 6,355,257, the disclosures of which are incorporated herein by reference in their entireties.

The invention also contemplates the use of a combination of adjuvants that stimulate both Th1 and Th2 types. In a preferred embodiment, the adjuvant that stimulates both Th1 and Th2 types is a saponin. Saponins are a heterogeneous group of sterol glycosides and triterpenoid glycosides that are found in the bark, leaves, stems, roots and even flowers of a wide range of plant species. Saponin from the bark of the Quillaia saponaria Molina tree have been widely studied as adjuvants. Saponin can also be commercially obtained from Smilax ornata (sarsaprilla), Gypsophilla paniculata (brides veil), and Saponaria officinalis (soap root). Saponin adjuvant formulations include purified formulations, such as QS21, as well as lipid formulations, such as ISCOMs. Saponin compositions have been purified using HPLC and RP-HPLC.

Specific purified fractions using these techniques have been identified, including QS7, QS17, QS18, QS21, QH-A, QH-B and QH-C. Preferably, the saponin is QS21. Saponin formulations may also comprise a sterol, such as cholesterol. Combinations of saponins and cholesterols can be used to form unique particles called immunostimulating complexes (ISCOMs). ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 45-47. Optionally, the ISCOMS may be devoid of additional detergent. A review of the development of saponin based adjuvants can be found in Barr et al. (Advanced Drug Delivery Reviews, 1998, 32:247-271) and Sjolanderet et al. (Advanced Drug Delivery Reviews, 1998, 32:321-338)

Conjugates according to the invention may have improved pharmacokinetic properties compared to unconjugated peptides. The pharmacokinetic properties of a peptide include, for example, its rate of absorption and excretion, its tissue distribution profile, its rate of metabolism and its toxicity. Typically, the conjugates of the invention have a decreased rate of excretion and/or an increased circulating half-life in vivo, compared to unconjugated peptides.

Preferred conjugates for use in the present invention include:

proteins comprising the administration to a subject in need thereof of a conjugate comprising a peptide derived from the C-terminal region of Aβ(1-42) and albumin or to a composition comprising a peptide derived from the C-terminal region of Aβ(1-42) and albumin and an adjuvant.

As used herein, the terms "treat", "treatment" and "treating" refer to the amelioration of one or more symptoms associated with a disease that results from the administration of a therapeutically effective amount of the composition of the invention or a pharmaceutical preparation comprising thereof, to a subject in need of said treatment. Thus, "treatment" as used herein covers any treatment of a disease, disorder or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; or (c) relieving the disease or condition, i.e., causing regression of the disease or condition or amelioration of one or more symptoms of the disease or condition. The population of subjects treated by the method includes a subject suffering from the undesirable condition or disease, as well as subjects at risk for development of the condition or disease. Thus, one of skill in the art realizes that a treatment may improve the patient's condition, but may not be a complete cure of the disease. As used herein, the terms "disorder" and "disease"

| Peptide | Carrier | Adjuvant |
|---|---|---|
| NH$_2$-MVGGVVIA-COOH (Aβ35-42) | Albumin | Rehydragel HPA |
| NH$_2$-GLMVGGVVIA-COOH (Aβ33-42) | Albumin | Rehydragel HPA |
| NH$_2$-MVGGVVIA-COOH (Aβ35-42) | Albumin | Abisco |
| NH$_2$-GLMVGGVVIA-COOH (Aβ33-42) | Albumin | Abisco |
| NH$_2$-CMVGGVVIA-COOH (Aβ35-42Cys) | Albumin | Rehydragel HPA |
| NH$_2$-CGLMVGGVVIA-COOH (Aβ33-42Cys) | Albumin | Rehydragel HPA |
| NH$_2$-CMVGGVVIA-COOH (Aβ35-42Cys) | Albumin | Abisco |
| NH$_2$-CGLMVGGVVIA-COOH (Aβ33-42Cys) | Albumin | Abisco |
| NH$_2$-CGLMVGGVV-COOH (Aβ33-40Cys) | Albumin | Rehydragel HPA |
| NH$_2$-CGLMVGGVV-COOH (Aβ33-40Cys) | Albumin | Abisco |

Therapeutic Methods of the Invention

As already mentioned at the beginning of the description, the composition of the present invention has proven to be useful in the treatment of a disease associated with deposition of amyloid proteins. Therefore, in another aspect, the invention relates to conjugate comprising a peptide derived from the C-terminal region of Aβ(1-42) and albumin or to a composition comprising a peptide derived from the C-terminal region of Aβ(1-42) and albumin and an adjuvant for the treatment of a disease associated with deposition of amyloid proteins.

In another aspect, the invention relates to conjugate comprising a peptide derived from the C-terminal region of Aβ(1-42) and albumin or to a composition comprising a peptide derived from the C-terminal region of Aβ(1-42) and albumin and an adjuvant for the manufacture of a medicament for the treatment of a disease associated with deposition of amyloid proteins.

In another aspect, the invention relates to a method for the treatment of a disease associated with deposition of amyloid are used interchangeably to refer to an abnormal or pathological condition in a subject that impairs bodily functions and can be deadly.

The phrase "therapeutically effective amount" is used herein to mean an amount sufficient to prevent, and preferably reduce by at least about 25 percent, more preferably by at least 50 percent, most preferably by at least 90 percent, a clinically significant change in a feature of pathology. As related to the present invention, the term may also mean an amount sufficient to ameliorate or reverse one or more symptoms associated with a disease associated with deposition of amyloid proteins, such as Alzheimer's disease. In particular, a "therapeutically effective amount" of the treatment may result in amelioration, reduction or elimination of at least one of the following symptoms: memory impairment, persistent sadness or anxiety, feelings of emptiness, hopelessness, pessimism, guilt, worthlessness, helplessness, a loss of interest or pleasure in hobbies and activities that were once enjoyed, decreased energy, or fatigue, difficulty concentrating, remembering, or making decisions, insomnia, early-morning awakening, or oversleeping, appetite and/or weight loss or overeating and weight gain, thoughts of death or suicide and suicide attempts, restlessness, irritability, and persistent physical symptoms that do not respond to treatment, such as headaches, digestive disorders, and chronic pain. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "subject" refers to an animal, preferably a mammal including a non-primate (e.g. a cow, pig, horse, cat, dog, rat, or mouse) and a primate (e.g. a monkey or a human). In a preferred embodiment, the subject is a dog. In a more preferred embodiment, the subject is a primate which, in a still more preferred embodiment, said primate is a human.

In the context of the present invention, "a disease associated with deposition of amyloid proteins" includes diseases associated with the accumulation of amyloid protein which can either be restricted to one organ, i.e. "localized amyloidosis" or spread to several organs, which is denoted "systemic amyloidosis". Diseases associated with deposition of amyloid proteins that can be treated with the compositions according to the present invention include, without limitation, the disease shown in Table 1.

| Disease | Featured protein |
| --- | --- |
| Alzheimer's disease | Beta amyloid |
| Inclusion body myositis (IBM), | Beta amyloid |
| Type 2 diabetes mellitus | IAPP (Amylin) |
| Parkinson's disease | Alpha-synuclein |
| Transmissible spongiform encephalopathy (Mad Cow Disease) | Prion |
| Huntington's Disease | Huntingtin |
| Medullary carcinoma of the thyroid | Calcitonin |
| Cardiac arrhythmias | Atrial natriuretic factor |
| Atherosclerosis | Apolipoprotein AI |
| Rheumatoid arthritis | Serum amyloid A |
| Aortic medial amyloid | Medin |
| Prolactinomas | Prolactin |
| Familial amyloid polyneuropathy | Transthyretin |
| Hereditary non-neuropathic systemic amyloidosis | Lysozyme |
| Dialysis related amyloidosis | β2-Microglobulin |
| Finnish amyloidosis | Gelsolin |
| Lattice corneal dystrophy | Keratoepithelin |
| Cerebral amyloid angiopathy | Beta amyloid |
| Cerebral amyloid angiopathy (Icelandic type) | Cystatin |
| Systemic AL amyloidosis | Immunoglobulin light chain AL |

Secondary amyloidosis may be associated with chronic infection (such as tuberculosis) or chronic inflammation (such as rheumatoid arthritis), including a familiar form of secondary amyloidosis which is also seen in Familial Mediterranean Fever (FMF) and another type of systemic amyloidosis found in long-term hemodialysis patients. Localized forms of amyloidosis include, without limitation, diabetes type II and any related disorders thereof, neurodegenerative diseases such as scrapie, bovine spongiform encephalitis, Creutzfeldt-Jakob disease, Alzheimer's disease, Cerebral Amyloid Angiopathy, and prion protein related disorders. The hallmark of amyloid diseases is the deposition in organs of amyloid plaques consisting mainly of fibrils, which, in turn, are composed of characteristic fibril proteins or peptides.

Therefore, in a particular embodiment, the disease associated with deposition of amyloid proteins is selected from Alzheimer's disease, Creutzfeldt-Jakob disease, Cerebral Amyloid Angiopathy and prion protein related disorders and muscle degeneration.

As the skilled person will understood, all the particular embodiments regarding the composition or kit of the invention for use in medicine are also applicable when said composition of kit is used for the treatment of a disease associated with deposition of amyloid proteins. Therefore, particular embodiments regarding the therapeutic methods of the invention using the conjugate or the composition are:

the peptide derived from the C-terminal region of Aβ(1-42) is selected from Aβ(35-42) (SEQ ID NO: 2), Aβ(33-42) (SEQ ID NO: 3) y Aβ(33-40) (SEQ ID NO: 4);

the peptide derived from Aβ(1-42) C-terminal region further comprises an additional N-terminal Cys;

the albumin is bovine serum albumin.

the adjuvant is, preferably, a Th1 or Th2 type adjuvant, and the composition of the invention or the active components from the kit of the invention is bi-weekly administered.

Detailed description of these particular embodiments can be found in previous paragraphs.

In another particular embodiment, the disease associated with deposition of amyloid protein is selected from Alzheimer's disease, Creutzfeldt-Jakob disease, Cerebral Amyloid Angiopathy, and prion protein related disorders.

The conjugate of the invention or the composition of the invention can be administered by different methods, e.g. intravenously, intraperitoneally, subcutaneously, intramuscularly, topically, intradermally, orally, intranasally or intrabronchially, as well as locally, systemically or directly to the target site (localized way). A review of the different methods of administration of active ingredients, of the excipients to be used and of the processes for manufacturing them can be found in Tratado de Farmacia Galénica, C. Faulí i Trillo, Luzán 5, S. A. de Ediciones, 1993 and in Remington's Pharmaceutical Sciences (A. R. Gennaro, Ed.), 20th edition, Williams & Wilkins PA, USA (2000).

In the present invention, a "localized way" is understood as the local administration of the conjugate of the invention to a specific place of the human or animal body. Preferably, the administration will be at a site where there is rapid blood flow, e.g., intravenously, peripheral or central vein. Other routes may find use where the administration is coupled with slow release techniques or a protective matrix. Also, mucosal immunization via nasal administration is a suitable method, since it is known that such a route of administration would favor a Th2 type response.

The dosage regimen will be determined by the doctor and the clinical factors. As it is well known in medicine, dosages depend on many factors including the physical characteristics of the patient (age, size, sex), the method of administration used, the severity of the disease, the particular compound used and the pharmacokinetic properties of the individual.

In a particular embodiment, the composition of the invention or the active components from the kit of the invention is bi-weekly administered.

The composition of the invention or the active components from the kit of the invention has proven to be useful for its use in medicine.

For use in medicine, the composition of the invention can be in the form of a prodrug, salt, solvate or clathrate, either in isolated form or in combination with additional active agents. The composition according to the present invention can be formulated together with an excipient which is acceptable from the pharmaceutical point of view. Preferred excipients for their use in the present invention include sugars, starches, celluloses, gums and proteins.

As the skilled person will understand, the composition of the invention can be formulated by conventional processes known in the state of the art in a solid (for example, tablets, capsules, sugar-coated tablets, granules, suppositories, crystalline or amorphous sterile solids which can be reconstituted to provide liquid forms, etc.), liquid (for example, solutions, suspensions, emulsions, elixirs, lotions, unguents etc.) or semisolid (gels, ointments, creams and the like) pharmaceutical dosage form. Examples of pharmaceutically acceptable carriers are known in the state of the art and include phosphate buffered saline solutions, water, emulsions such as oil/water emulsions, different types of wetting agents, sterile solutions, etc.

The following methods and examples are to be construed as illustrative and not limitative of the scope of the invention.

EXAMPLES

Immunization of Dogs with C-Terminal Sequences of Beta-Amyloid Protein is Safe and Depletes the Protein from the Blood Example 1

Immunization with Aβ(x-42) Peptides

I. Materials and Methods

1. Characteristics of the animals

Twelve aged Beagles dogs of either sex were used in this invention. The characteristics of the animals are summarized in Table 1. They came from commercial sources and had been living in the kennels of the University of Santiago for breeding. During the experiment, the animals were housed in three collective kennels with free indoor/outdoor access and were supplied with a formulated dog food and water ad libitum. The animals were thoroughly recognized just before the beginning of the experiments, including physical and neurological examination, blood biochemistry values and hemogram, and were declared healthy.

The animals were allocated in four groups (A, B, C and D; n=3) by a veterinary clinician blinded to the treatment eventually assigned to each group. The animals were explored every week for the apparition of any clinical sign of reaction to the vaccines. An additional complete recognition including again blood biochemistry and haemogram was carried out after the third immunization.

The animals were treated according to the European and Spanish legislations on animal handling (86/609/EU, Real Decreto 1201/2005) and every effort was done to minimize the suffering of the animals. The study was approved by the Ethical Committee of the University of Santiago.

2. Preparation of the Immunogens

A synthetic Aβ(35-42) peptide (with an additional N-terminal Cys when conjugated via SPDP) as antigen (0.4 mg/injection) incorporated in four different vaccine formulations were used for the immunization of the animals. Each of these formulation combined a protein carrier, either blue carrier (BC; Pierce, Rockford, Ill.; groups A and B) or bovine serum albumin (BSA; Sigma, Madrid, Spain; groups C and D); and an adjuvant, either rehydragel HPA (RH; Quimibios (the manufacturer is Reheis), Barcelona, Spain; groups A and C) or Abisco-300 (AB; Isconova AB, Uppsala Science Park, SE-751 83 Uppsala, SWEDEN; groups B and D).

2.1. Coupling Synthetic Peptides to BSA Using SPDP:

First, a stock solution of 20 mM SPDP (N-succinimidyl 3-(2-pyridyldithio) propionate; 50 mg/8 ml DMSO) was prepared. Then, 5 mg of BSA were dissolved in 1 ml of PBS/5 mM EDTA pH 8 and 50 µl of the 20 mM SPDP solution were added to the BSA. The solution was incubated for 2 hours at room temperature. After this, a desalting column was equilibrated with PBS/EDTA and the buffer exchange to the SPDP-modified BSA to remove reaction byproducts and excess non-reacted SPDP reagent.

Next, the level of SPDP-modification was determined using the following protocol:
a) Dilute 100 µl of SPDP-modified and desalted BSA to 1 ml with PBS.
b) Measure and record the absorbance at 343 nm of the protein simple compared to PBS/EDTA blank (test in triplicate).
c) Add 10 µl of 15 mg/ml DTT to the 1 ml SPDP-modified protein sample, mix.
d) After exactly 15 minutes, measure and record the absorbance at 343 nm of the reduced sample.
e) Use the following equation:

$$\frac{(Ave.A343 \text{ after } DTT) - (Ave.A343 \text{ before } DTT)}{8080} \times \frac{MW BSA}{\frac{mg}{ml} \text{ of } BSA} = X$$

If X is between 5 and 6'S, 2 mg of synthetic peptide is added to the 5 mg of SPDP-modified BSA.

After the level of SPDP-modification was determined, the reaction mixture was incubated with agitation 18-24 hours overnight, and the reaction mixture was freeze-dry.

2.2. Coupling Synthetic Peptides to Blue Carrier Using Glutaraldehyde:

2 ml borate buffer pH 10 and 66 µl (200 mg/ml) of Blue Carrier were added to a reaction vial and mixed gently. Next, 12 mg of the synthetic peptide were added to the reaction vial. Simultaneously, glutaraldehyde was diluted to 0.3% by adding borate buffer pH 10.

Next, 1 ml of freshly prepared 0.3% glutaraldehyde solution was slowly added to the reaction vial while stirring at room temperature, allowing 2 hours to react at room temperature in the dark (the solution turned yellow). In order to block the unreacted glutaraldehyde, 250 µl of glycine 1M were added to the reaction vial and mixed gently, incubating at room temperature for additional 30 minutes. After this the reaction mixture was transferred to the desalting column equilibrated with PBS. The reaction mixture was freeze-dry and dissolved to a suitable concentration.

Thus the four different formulations used in this invention were as follow:
A) 400 micrograms of Abeta35-42 conjugated to Blue Carrier plus 200 microliters of Rehydragel HPA.
B) 400 micrograms of Abeta35-42 conjugated to Blue Carrier plus 200 microliters of Abisco-300.
C) 400 micrograms of Abeta35-42 conjugated to BSA plus 200 microliters of Rehydragel HPA.
D) 400 micrograms of Abeta35-42 conjugated to BSA plus 37 microliters of Abisco-300.

The synthetic peptides used were:
When conjugated to Blue Carrier with glutaraldehyde:
1. Aβ(35-42) ($NH_2$-MVGGVVIA-COOH) (SEQ ID NO: 2) in dogs (and mice; see below)
2. Aβ(33-42) ($NH_2$-GLMVGGVVIA-COOH) (SEQ ID NO: 3) in rabbits (see below)

When conjugated to BSA with SPDP:
1. ABcys-(35-42) ($NH_2$—CMVGGVVIA-COOH) (SEQ ID NO: 17) in dogs (and mice; see below)
2. ABcys-(33-42) ($NH_2$—CGLMVGGVVIA-COOH) (SEQ ID NO:18) in rabbits (see below)

3. Immunizing Protocol and Blood Sampling

Animals (dogs) were separated in 4 groups and assigned to any of the four vaccine formulations. Animals were immunized with Abeta 35-42 subcutaneously in the back and monitored for adverse reactions. The schedule for immunization and sampling is represented in FIG. 1 (A). In short, the animals were injected biweekly for seven times. Dogs in groups C and D received an additional 8th immunization seven months after the seventh injection.

Blood samples were collected from the jugular vein into polypropylene vials with EDTA and protease inhibitors (complete mini mg/10 ml, Roche) just before the first immunization (W0), and a week after the third (at week 5: W5), fifth (W9), and seventh (W13) immunizations (FIG. 1). Additional blood samples were obtained from the animals of the groups C and D four months after the seventh immunization (W31), and the first and third week after the booster immunization (W43 and W45, respectively).

The samples were gently mixed and preserved at 4° C. for a maximum of 2 hours before centrifugation at 4000 g during 10 minutes. Then the plasma was aliquoted and frozen at −80° C. until used. Additionally, in each extraction, ~1 ml of blood from every animal was collected in an EDTA-free polypropylene vial for obtaining the serum. This sample was allowed to clot for one hour at room temperature, then centrifuged at 4000 g 10 minutes and the serum collected and preserved at −80° C. until essayed for blood biochemistry determinations.

Samples of cerebrospinal fluid (CSF) were collected under general anesthesia and aseptic conditions a week before the first and at week $13^{th}$, after the seventh immunization (FIG. 1). These CSF samples were aliquoted and frozen at −80° C. until used.

4. Anti-Aβ-Antibodies Assays in Plasma and CSF

Anti Aβ-antibodies were determined by direct ELISA in 96 wells polypropylene plates. Microtiter wells were coated with 2.5 μg/ml of human Aβ(1-42) peptide (#24224 AnaSpec. San Jose, Calif., USA) in 100 mM sodium bicarbonate and 2M guanidine hydrochloride buffer (pH 9.6) at 4° C. overnight. The plates were then washed three times with 300 μl of washing buffer (0.5 M Tris, 1.5 M sodium chloride, 0.5% Tween20; pH 8); blocked with 300 μl of blocking buffer (0.05 M Tris, 0.2% Tween20, 0.5% BSA; pH 8) for two hours at 37° C. and washed again another three times. The coated plates were incubated for one hour at 37° C. with 100 μl of three fold serial dilutions of the dog plasmas in vehicle buffer (0.05 M Tris, 0.5 M sodium chloride, 0.05% BSA, 0.05% Tween20; pH 8) in a row of 10 wells starting with a 1:30 dilution of the plasma in the first well. The greatest plasma dilution assayed was $1/10 \times 3^{10}$. The eleventh and twelfth column in each plate was filled with vehicle buffer without plasma for the blank controls. Then the plates were washed and incubated for one hour at 37° C. with 100 μl of a 1:1000 dilution in vehicle buffer of a horse radix peroxidase-conjugated rabbit anti-dog IgG (Jackson ImmunoResearch. Suffolk, UK), washed three times, and incubated with 0.0375% of ABTS (Roche, Barcelona, Spain) in buffer for ABTS (Roche. Barcelona, Spain). The absorbance at 405 nm was read on an automated plate reader (Synergy 4, Biotek. Winooski, Vt., USA).

Plasma anti-Aβ antibody concentrations were calculated using the monoclonal 6E10 antibody as a standard on the same ELISA plates and are expressed in μg/μl. The EC50 of each plasma sample was determined by the nonlinear regression of the absorbance to the logarithm of the dilutions in each well (GraphPad Prism 3.02). In addition, the plasma endpoint titer was defined as the maximal plasma dilution in which absorbance was three times higher than the mean absorbance of the blank wells.

Determination of Free Aβ Peptides in Plasma

Levels of Aβ1-42 and Aβ1-40 in the plasma and CSF of the dogs were measured using indirect sandwich ELISA with the ABtest-40 and ABtest-42 ELISA kits from Araclon Biotech (Zaragoza, Spain) following the instructions of the manufacturer.

II. Results

The animals remained healthy and active throughout the whole time of the experiment. In particular, no sign of reaction to the vaccines was detected. Mean body weight increment from week 0 to week $13^{th}$ was 1±1.7 Kg (Table 1). Only two animals lost body weight in that period (1 Kg each, which represents a 4% and a 7% of their weight at week 0, respectively).

TABLE 1

Characteristics of the animals

| Group/Dog | Sex | Age (years) | Weight (Kg) at W0 | Weight (Kg) at W13 | Weight increment (Kg) | % of weight variation |
|---|---|---|---|---|---|---|
| A1 | female | 11 | 16 | 18 | 2 | 12.50 |
| A2 | male | 6 | 23 | 22 | −1 | −4.35 |
| A3 | male | 8 | 22 | 23.45 | 1.45 | 6.59 |
| B1 | female | 10 | 13 | 13 | 0 | 0.00 |
| B2 | male | 6 | 21 | 23 | 2 | 9.52 |
| B3 | male | 12 | 24.45 | 26.7 | 2.25 | 9.20 |
| C1 | female | 6 | 18 | 18 | 0 | 0.00 |
| C2 | male | 6 | 16 | 16 | 0 | 0.00 |
| C3 | male | 10 | 24.5 | 29 | 4.5 | 18.37 |
| D1 | male | 6 | 14 | 13 | −1 | −7.14 |
| D2 | male | 6 | 15 | 15 | 0 | 0.00 |
| D3 | male | 10 | 18.7 | 21.5 | 2.8 | 14.97 |
| | mean | | 18.80 | 19.89 | 1.08 | 4.97 |
| | SD | | 4.10 | 5.22 | 1.68 | 8.03 |

1. Anti-Aβ(1-42)Antibody Titers

Groups A and B

Interpolation of the plasma absorbance of the animals within group A and B against the 6E10 standard did not detect consistent differences between the pre-immune samples and the samples collected at W5, W9 and W13 (Table 2A and FIG. 2A). The factor of increment in plasma antibody titers, measured as equivalency to μg/μl of 6E10, after three and seven immunizations (W5 and W13, respectively) were very low (0.8±0.2 and 0.8±0.2, respectively for group A; and 1.2±0.1 and 1.3±0.3, respectively for group B. Table 3). The values of plasma $EC_{50}$ for the specific antibody (anti-Aβ42) in animals within group A and B were very low from week 0 to week 13. Indeed, the values of plasma $EC_{50}$ decreased from W0 to W5 in all these dogs, with the exception of the dog B2 which showed an insignificant increment exclusively at this time point (Table 2B and FIG. 2A-C). In addition, not even the most concentrated plasma dilution (1:30) of these dogs after immunizations gave an absorbance three times higher than that measured in the pre-immune plasma samples (Table 2C). Thus, dogs in these two groups were considered non-responder to their corresponding vaccine formulations (A and B).

TABLE 2

Plasma titers of specific anti-Aβ42 antibodies at different time points

| Group/Dog | W0 | W5 | W9 | W13 | W31 | W43 | W45 |
|---|---|---|---|---|---|---|---|
| Panel A: equivalent to µg/µl of the monoclonal antibody 6E10. | | | | | | | |
| A1 | 0.0028 | 0.0016 | 0.0015 | 0.0016 | | | |
| A2 | 0.0024 | 0.0023 | 0.0018 | 0.0023 | | | |
| A3 | 0.0027 | 0.0022 | 0.0028 | 0.0021 | | | |
| B1 | 0.0019 | 0.0023 | 0.0070 | 0.0033 | | | |
| B2 | 0.0025 | 0.0031 | 0.0022 | 0.0028 | | | |
| B3 | 0.0027 | 0.0028 | 0.0029 | 0.0032 | | | |
| C1 | 0.0016 | 0.0205 | 0.0147 | 0.0084 | 0.0008 | 0.0017 | 0.0019 |
| C2 | 0.0010 | 0.0113 | 0.0083 | 0.0093 | 0.0007 | 0.0040 | 0.0041 |
| C3 | 0.0022 | 0.0276 | 0.0214 | 0.0206 | 0.0021 | 0.0089 | 0.0102 |
| D1 | 0.0025 | 0.1075 | 0.0933 | 0.1048 | 0.0076 | 0.0716 | 0.0520 |
| D2 | 0.0017 | 0.0529 | 0.0406 | 0.0294 | 0.0028 | 0.0229 | 0.0164 |
| D3 | 0.0019 | 0.0321 | 0.0138 | 0.0256 | 0.0024 | 0.0088 | 0.0071 |
| Panel B: values of plasma EC50 for the specific antibody (anti-Aβ42) | | | | | | | |
| A1 | 49 | 42 | 35 | 29 | | | |
| A2 | 170 | 85 | 158 | 133 | | | |
| A3 | 155 | 111 | 132 | 115 | | | |
| B1 | 51 | 47 | 235 | 66 | | | |
| B2 | 186 | 253 | 123 | 93 | | | |
| B3 | 79 | 60 | 41 | 59 | | | |
| C1 | 45 | 773 | 722 | 385 | 68 | 46 | 49 |
| C2 | 147 | 473 | 350 | 385 | 70 | 114 | 129 |
| C3 | 123 | 1349 | 994 | 853 | 70 | 336 | 460 |
| D1 | 51 | 6759 | 5738 | 6302 | 319 | 4202 | 2733 |
| D2 | 53 | 2956 | 2021 | 1378 | 66 | 1122 | 790 |
| D3 | 57 | 1550 | 752 | 1169 | 61 | 365 | 267 |
| Panel C: the inverse of the maximal dilution of plasma with an absorbance 3X higher than the blank wells | | | | | | | |
| A1 | 270 | 270 | 90 | 270 | | | |
| A2 | 270 | 270 | 270 | 270 | | | |
| A3 | 270 | 270 | 270 | 270 | | | |
| B1 | 270 | 270 | 810 | 810 | | | |
| B2 | 270 | 810 | 270 | 270 | | | |
| B3 | 270 | 270 | 270 | 270 | | | |
| C1 | 90 | 2430 | 2430 | 2430 | 270 | 270 | 270 |
| C2 | 90 | 2430 | 2430 | 2430 | 90 | 810 | 810 |
| C3 | 270 | 2430 | 2430 | 2430 | 810 | 2430 | 2430 |
| D1 | 270 | 21870 | 21870 | 21870 | 2430 | 21870 | 7290 |
| D2 | 270 | 7290 | 7290 | 7290 | 810 | 7290 | 2430 |
| D3 | 270 | 7290 | 2430 | 7290 | 810 | 2430 | 810 |

TABLE 3

Factor of increment respect to the pre-immune plasma (equivalency to µg/µl of 6E10)

| Group/Dog | W0/W0 | W5/W0 | W9/W0 | W13/W0 | W31/W0 | W43/W0 | W45/W0 |
|---|---|---|---|---|---|---|---|
| A1 | 1.0 | 0.6 | 0.5 | 0.6 | | | |
| A2 | 1.0 | 1.0 | 0.8 | 1.0 | | | |
| A3 | 1.0 | 0.8 | 1.0 | 0.8 | | | |
| mean ± SD | 1.0 ± 0.0 | 0.8 ± 0.2 | 0.8 ± 0.3 | 0.8 ± 0.2 | | | |
| B1 | 1.0 | 1.2 | 3.6 | 1.7 | | | |
| B2 | 1.0 | 1.2 | 0.9 | 1.1 | | | |
| B3 | 1.0 | 1.1 | 1.1 | 1.2 | | | |
| mean ± SD | 1.0 ± 0.0 | 1.2 ± 0.1 | 1.9 ± 1.5 | 1.3 ± 0.3 | | | |
| C1 | 1.0 | 12.5 | 8.9 | 5.1 | 0.5 | 1.0 | 1.1 |
| C2 | 1.0 | 11.8 | 8.6 | 9.7 | 0.7 | 4.2 | 4.2 |
| C3 | 1.0 | 12.6 | 9.7 | 9.4 | 1.0 | 4.1 | 4.6 |
| mean ± SD | 1.0 ± 0.0 | 12.3 ± 0.4 | 9.1 ± 0.6 | 8.1 ± 2.6 | 0.7 ± 0.2 | 3.1 ± 1.8 | 3.3 ± 1.9 |
| D1 | 1.0 | 42.8 | 37.2 | 41.7 | 3.0 | 28.5 | 20.7 |
| D2 | 1.0 | 30.6 | 23.5 | 17.0 | 1.6 | 13.2 | 9.5 |
| D3 | 1.0 | 17.1 | 7.4 | 13.7 | 1.3 | 4.7 | 3.8 |
| mean ± SD | 1.0 ± 0.0 | 30.2 ± 12.8 | 22.7 ± 14.9 | 24.1 ± 15.3 | 2.0 ± 0.9 | 15.5 ± 12.1 | 11.3 ± 8.6 |

Groups C and D

In contrast with the observed in groups A and B, the dogs treated with the vaccine formulations C and D showed substantial modifications in their plasma antibody titers. The response of all the dogs in these two groups, as measured by the 6E10 standard, the $EC_{50}$ or the end-point dilution, followed the same pattern although quantitative differences were observed both, inter- and intra-groups (Table 2A-C). The general pattern was characterized by a substantial increase of the titers after three immunizations that were maintained with only slight modifications from W5 to W13 (FIGS. 2A-C). Thus, antibody titers were substantially increased after three immunizations but did not increased substantially (or even slightly decreased) after the subsequent four biweekly vaccine injections. In concrete the titers, measured as equivalency to μg/μl of 6E10, after three and seven immunizations (W5 and W13, respectively) were multiplied by a factor of 12.3±0.4 and 8.1±2.6, respectively for group C; and 30.2±12.8 and 24.1±15.3, respectively for group D. Table 3)

Figure 2:
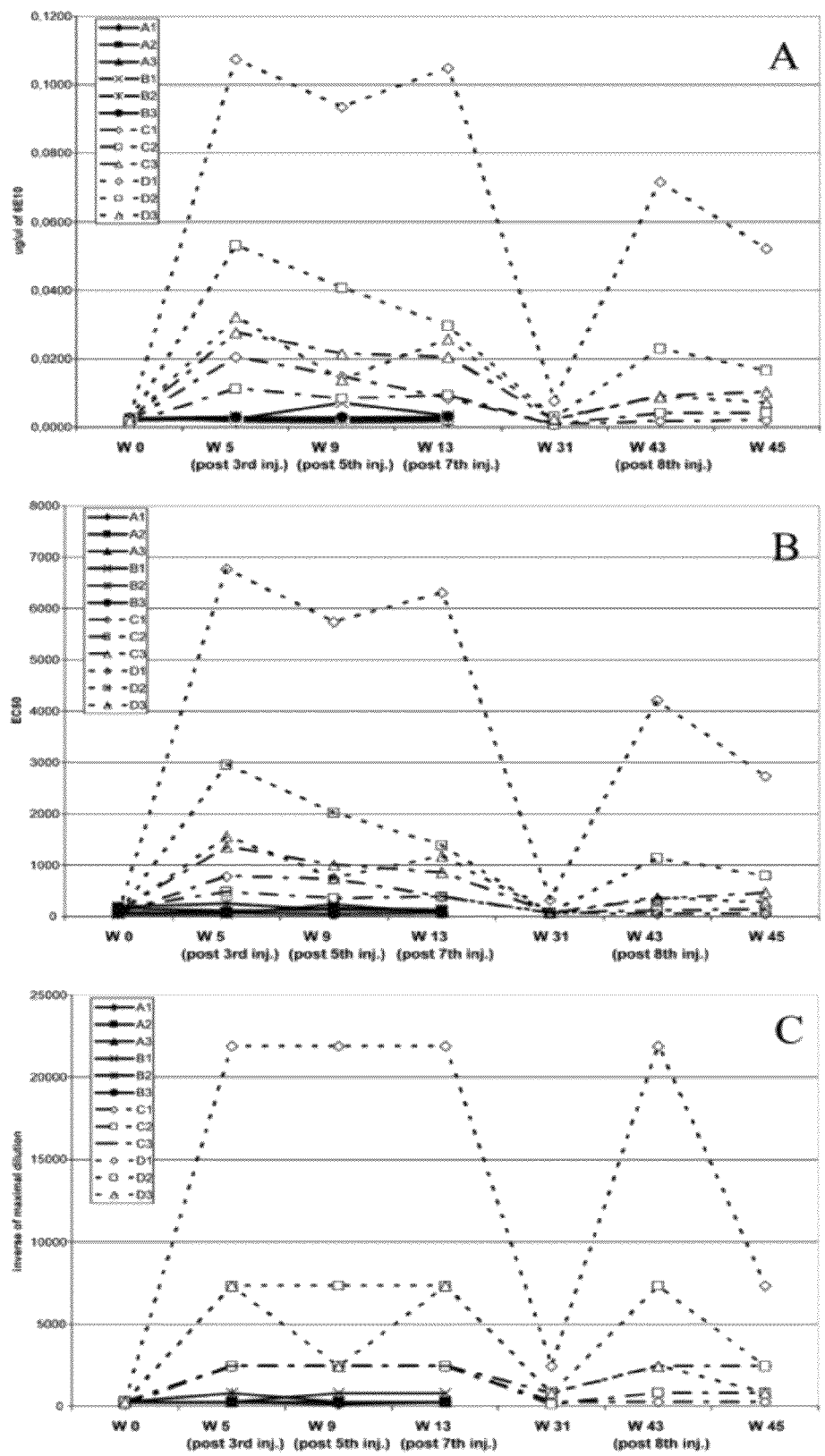
FIG. 2: (A-C). Evolution of the plasma anti-Aβ antibody titers. A) The anti-Aβ antibody titers of the plasma samples are expressed as equivalent to μg/μl of the monoclonal antibody 6E10. B) The anti-Aβ antibody titers of the plasma samples are expressed by their EC50. D) The anti-Aβ antibody titers of the plasma samples are expressed by the inverse of the maximal plasma dilution in which absorbance was three times higher than the mean absorbance of the blank wells. The different time points (in weeks) are represented in the horizontal axis. Each line represents one animal as indicated in the legend. The formulations received by each group of animals is synthetic peptide—Blue Carrier plus Rehydragel HPA (A) synthetic peptide—Blue Carrier plus Abisco-300 (B); synthetic peptide—BSA plus Rehydragel HPA (C) and synthetic peptide—BSA plus Abisco-300 (D). The shorter continuous lines correspond to the non-responder animals (groups A and B) in which treatment was halted at week 13th. Animals in group C are represented by broken lines and the corresponding individual symbol. Those in group D are represented by dotted lines and the corresponding individual symbol.
Figure 3:
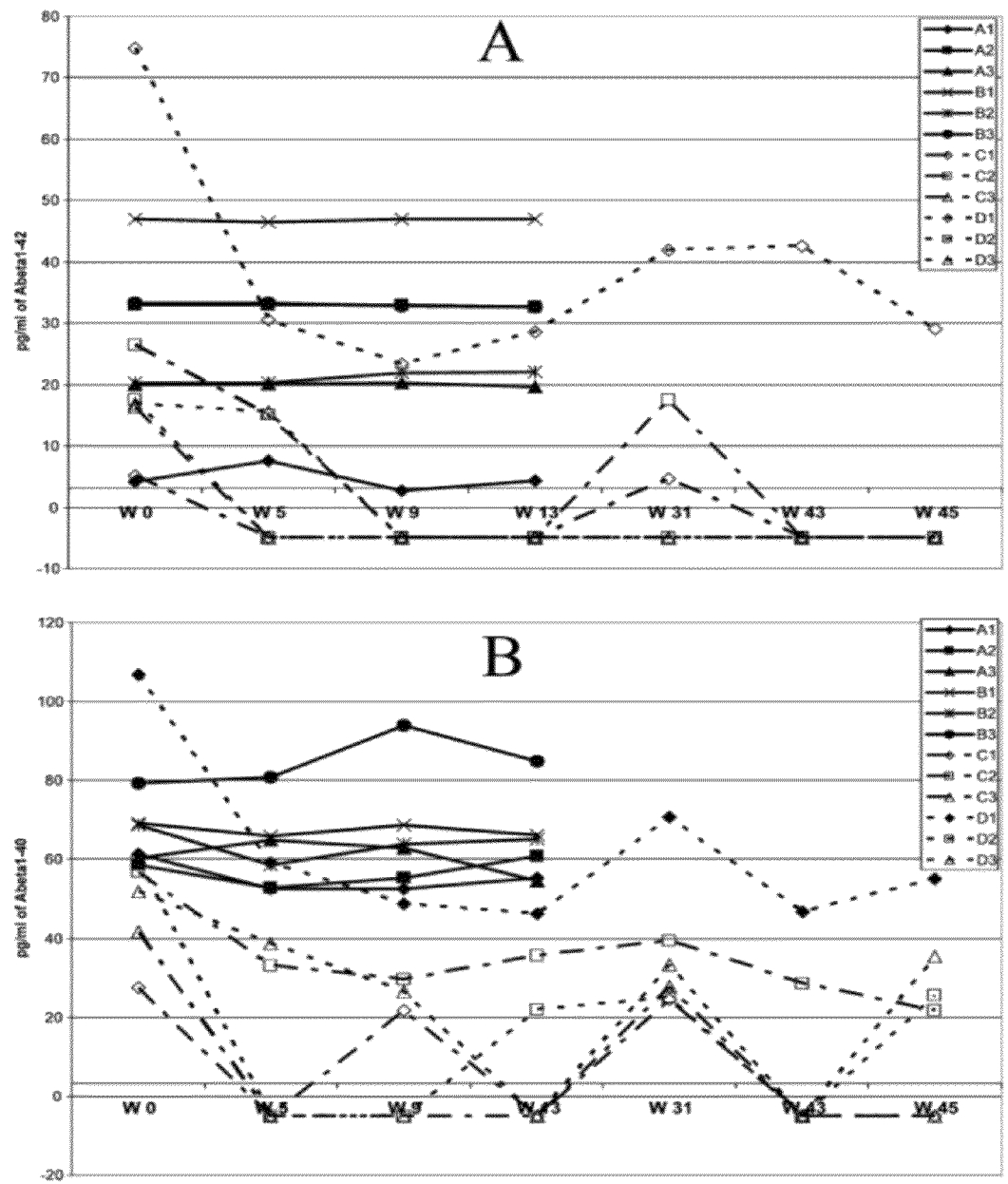
FIG. 3 (A-B). Evolution of the plasma Aβ-peptide concentrations. A) represent the evolution at different time points of the plasma concentration of Aβ 1-42 peptide. B) represent the evolution at different time points of the plasma concentration of Aβ1-40 peptide. The horizontal axis crosses the Y axis at 3.125 pg/ml. The values below 3.125 have been represented as −5 pg/ml for the sake of clarity in the graph. The different time points (in weeks) are represented in the horizontal axis. Each line represents one animal as indicated in the legend. Each of the four groups (A, B, C, and D) received a different vaccine formulation. The shorter continuous lines correspond to the non-responder animals (groups A and B) in which treatment was halted at week $13^{th}$. Animals in group C are represented by broken lines and the corresponding individual symbol. Those in group D are represented by dotted lines and the corresponding individual symbol.

Four months after the last immunization (W31) the titers had fallen to very low levels (Table 2). However in the dogs of group D they were still two times higher than in the pre-immune plasma (Table 3). Then the dogs in groups C and D received an additional eighth immunization, carried out seven month after the seventh, with the corresponding vaccine formulation. This booster injection was followed by a substantial increase of the antibody titers in group D (15.5±12.1 times increased with regard to pre-immune plasma, Table 3) and, in a lesser degree, in group C (3.1±1.8 times increased with regard to pre-immune plasma, Table 3) (FIGS. 2A-C). In general, at any time point, antibody titers were always higher in the animals of the group D than in those of the group C. Nevertheless, the increments in the titers of the dog with the smaller response in group D (case D3) were very similar to the increments in the titers of the dogs in group C (Table 3, FIGS. 2, 3).

2. Aβ Peptide Titers

The sandwich ELISA did not detect consistent differences in the concentration of Aβ1-42 or Aβ1-40 peptides between the pre-immune plasma and the samples collected at W5, W9 and W13 in the animals of the non-responder groups (A and B) (Table 4A-B, FIGS. 3A-B). The factor of change in plasma Aβ1-42 concentration after three and seven immunizations (W5 and W13, respectively) was very low (1.2±0.7 and 1.0±0.0, respectively for group A; and 0.9±0.0 and 1.0±0.1, respectively for group B. Table 5A). Similarly, the factor of change in plasma Aβ1-40 concentration after three and seven immunizations (W5 and W13, respectively) was very low (0.9±0.1 for both weeks and both groups. Table 5B).

TABLE 4A

Concentration of peptide Aβ1-42 in pg/ml.

| Group/Dog | W0 | W5 | W9 | W13 | W31 | W43 | W45 | CSF W0 | CSF W13 |
|---|---|---|---|---|---|---|---|---|---|
| A1 | 4.16 | 7.50 | 2.76 | 4.31 | | | | 556.85 | 509.70 |
| A2 | 32.92 | 32.92 | 32.92 | 32.71 | | | | 253.06 | 322.77 |
| A3 | 19.98 | 20.07 | 20.24 | 19.62 | | | | 421.88 | 300.12 |
| B1 | 47.00 | 46.40 | 47.00 | 47.00 | | | | 299.86 | 420.84 |
| B2 | 20.33 | 20.33 | 21.83 | 22.01 | | | | 283.94 | 367.18 |
| B3 | 33.33 | 33.33 | 32.82 | 32.71 | | | | 314.82 | 228.06 |
| C1 | 5.20 | <3.125 | <3.125 | <3.125 | 4.70 | <3.125 | <3.125 | 718.84 | 532.56 |
| C2 | 26.46 | 15.00 | <3.125 | <3.125 | 17.53 | <3.125 | <3.125 | 519.74 | 581.28 |
| C3 | 16.35 | <3.125 | <3.125 | <3.125 | <3.125 | <3.125 | <3.125 | 671.03 | 649.07 |
| D1 | 74.76 | 30.58 | 23.33 | 28.60 | 41.96 | 42.62 | 29.10 | 677.44 | 731.28 |
| D2 | 17.56 | <3.125 | <3.125 | <3.125 | <3.125 | <3.125 | <3.125 | 783.95 | 888.61 |
| D3 | 16.85 | 15.51 | <3.125 | <3.125 | <3.125 | <3.125 | <3.125 | 488.97 | 762.05 |

TABLE 4B

Concentration of peptide Aβ1-40 in pg/ml.

| Group/Dog | W0 | W5 | W9 | W13 | W31 | W43 | W45 | CSF W0 | CSF W13 |
|---|---|---|---|---|---|---|---|---|---|
| A1 | 61.29 | 52.55 | 52.55 | 55.19 | | | | 3633.96 | 3831.76 |
| A2 | 58.67 | 52.76 | 55.21 | 60.84 | | | | 2269.62 | 2719.62 |
| A3 | 60.26 | 64.88 | 63.00 | 54.64 | | | | 2534.52 | 2822.02 |
| B1 | 104.31 | 38.70 | 39.86 | <3.125 | | | | 2890.55 | 3586.15 |
| B2 | 68.77 | 58.67 | 63.87 | 65.16 | | | | 2371.54 | 2610.96 |
| B3 | 79.30 | 80.89 | 93.87 | 84.78 | | | | 2449.42 | 2273.46 |
| C1 | 27.47 | <3.125 | 21.72 | <3.125 | 24.44 | <3.125 | <3.125 | 3503.87 | 2711.61 |
| C2 | 56.89 | 33.03 | 29.62 | 35.53 | 39.39 | 28.49 | 21.67 | 2632.58 | 3416.45 |
| C3 | 41.67 | <3.125 | <3.125 | <3.125 | 27.80 | <3.125 | <3.125 | 3121.29 | 2945.81 |
| D1 | 106.94 | 59.06 | 48.69 | 46.14 | 70.71 | 46.78 | 55.07 | 3139.03 | 3206.77 |
| D2 | 59.70 | <3.125 | <3.125 | 22.04 | 24.92 | <3.125 | 25.55 | 3737.74 | 3426.45 |
| D3 | 51.67 | 38.71 | 26.44 | <3.125 | 33.26 | <3.125 | 35.30 | 2955.16 | 3214.84 |

TABLE 5A

Factor of increments in peptide Abeta 1-42 with respect to the pre-immune plasma

| Group/Dog | W0/W0 | W5/W0 | W9/W0 | W13/W0 | W31/W0 | W43/W0 | W45/W0 |
|---|---|---|---|---|---|---|---|
| A1 | 1.0 | 1.8 | 0.7 | 1.0 | | | |
| A2 | 1.0 | 1.0 | 1.0 | 1.0 | | | |
| A3 | 1.0 | 1.0 | 1.0 | 1.0 | | | |
| mean ± SD | 1.0 ± 0.0 | 1.2 ± 0.5 | 0.8 ± 0.2 | 1.0 ± 0.0 | | | |
| B1 | 1.0 | 1.0 | 1.0 | 1.0 | | | |
| B2 | 1.0 | 1.0 | 1.1 | 1.1 | | | |
| B3 | 1.0 | 1.0 | 1.0 | 1.0 | | | |
| mean ± SD | 1.0 ± 0.0 | 0.9 ± 0.0 | 1.0 ± 0.0 | 1.0 ± 0.1 | | | |

TABLE 5A-continued

Factor of increments in peptide Abeta 1-42 with respect to the pre-immune plasma

| Group/Dog | W0/W0 | W5/W0 | W9/W0 | W13/W0 | W31/W0 | W43/W0 | W45/W0 |
|---|---|---|---|---|---|---|---|
| C1 | 1.0 | 0.2 | 0.2 | 0.2 | 0.9 | 0.2 | 0.2 |
| C2 | 1.0 | 0.6 | 0.0 | 0.0 | 0.7 | 0.0 | 0.0 |
| C3 | 1.0 | 0.1 | 0.1 | 0.1 | 0.1 | 0.1 | 0.1 |
| mean ± SD | 1.0 ± 0.0 | 0.2 ± 0.3 | 0.0 ± 0.1 | 0.0 ± 0.1 | 0.5 ± 0.1 | 0.0 ± 0.1 | 0.0 ± 0.1 |
| D1 | 1.0 | 0.4 | 0.3 | 0.4 | 0.6 | 0.6 | 0.4 |
| D2 | 1.0 | 0.1 | 0.1 | 0.1 | 0.1 | 0.1 | 0.1 |
| D3 | 1.0 | 0.9 | 0.1 | 0.1 | 0.1 | 0.1 | 0.1 |
| mean ± SD | 1.0 ± 0.0 | 0.4 ± 0.4 | 0.1 ± 0.1 | 0.1 v 0.2 | 0.2 ± 0.3 | 0.2 ± 0.3 | 0.1 ± 0.2 |

TABLE 5B

Factor of increments in peptide Abeta 1-40 with respect to the pre-immune plasma

| Group/Dog | W0/W0 | W5/W0 | W9/W0 | W13/W0 | W31/W0 | W43/W0 | W45/W0 |
|---|---|---|---|---|---|---|---|
| A1 | 1.0 | 0.9 | 0.9 | 0.9 | | | |
| A2 | 1.0 | 0.9 | 0.9 | 1.0 | | | |
| A3 | 1.0 | 1.1 | 1.0 | 0.9 | | | |
| mean ± SD | 1.0 ± 0.0 | 0.9 ± 0.1 | 0.9 ± 0.1 | 0.9 ± 0.1 | | | |
| B1 | 1.0 | 1.0 | 1.0 | 1.0 | | | |
| B2 | 1.0 | 0.9 | 0.9 | 0.9 | | | |
| B3 | 1.0 | 1.0 | 1.2 | 1.1 | | | |
| mean ± SD | 1.0 ± 0.0 | 0.9 ± 0.1 | 1.0 v 0.1 | 0.9 v 0.1 | | | |
| C1 | 1.0 | 0.0 | 0.8 | 0.0 | 0.9 | 0.0 | 0.0 |
| C2 | 1.0 | 0.6 | 0.5 | 0.6 | 0.7 | 0.5 | 0.4 |
| C3 | 1.0 | 0.0 | 0.0 | 0.0 | 0.7 | 0.0 | 0.0 |
| mean ± SD | 1.0 ± 0.0 | 0.2 ± 0.3 | 0.4 ± 0.4 | 0.2 ± 0.3 | 0.7 ± 0.1 | 0.1 ± 0.3 | 0.1 ± 0.2 |
| D1 | 1.0 | 0.6 | 0.5 | 0.4 | 0.7 | 0.4 | 0.5 |
| D2 | 1.0 | 0.0 | 0.0 | 0.4 | 0.4 | 0.0 | 0.4 |
| D3 | 1.0 | 0.7 | 0.5 | 0.0 | 0.6 | 0.0 | 0.7 |
| mean ± SD | 1.0 ± 0.0 | 0.4 ± 0.4 | 0.3 ± 0.3 | 0.2 ± 0.2 | 0.5 ± 0.1 | 0.1 ± 0.2 | 0.5 ± 0.1 |

Figure 4:
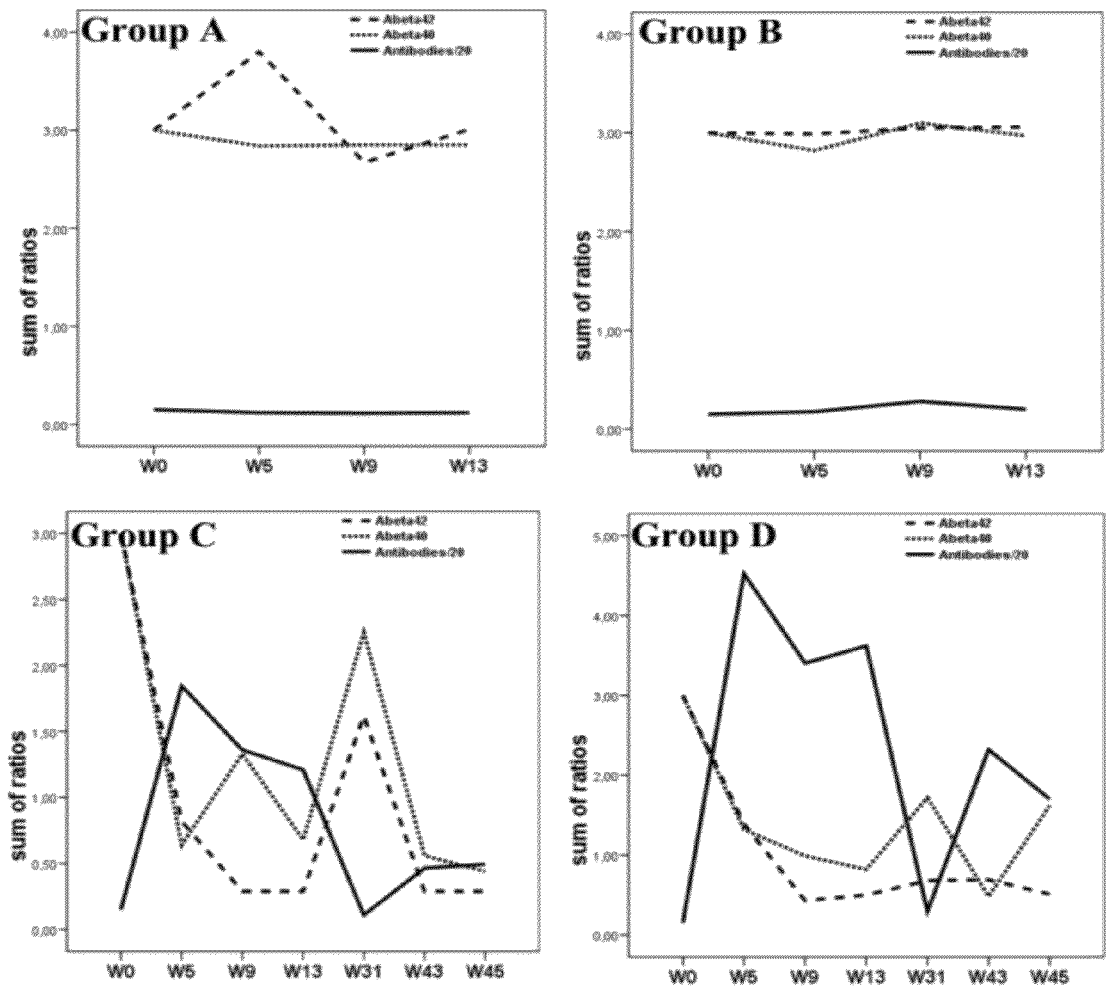
FIG. 4. Evolution of the ratios of change of plasma antibody titers and peptide concentrations with regard to the pre-immune state for each experimental group. Time points (in weeks) are represented in the horizontal axis. Broken line represents the evolution of the ratio of the plasma concentration of Aβ1-42 peptide at different time point with regard to the pre-immune state (W0). Dotted line represents the evolution of the ratio of the plasma concentration of Aβ1-40 peptide at different time point with regard to the pre-immune state (W0). Continuous line represents the evolution of the ratio of the plasma anti-Aβ antibody titers at different time point with regard to the pre-immune state (W0). For every ratio, the values in the vertical axis represent the sum of the three animals in the group. The values of the ratio of plasma anti-Aβ antibody titers has been divided by twenty for the clarity of the graphs.

In contrast with the observed in groups A and B, the dogs treated with the vaccine formulations C and D showed substantial modifications in their plasma Aβ(1-42) concentrations. These change followed a pattern characterized by a substantial decrease of the Aβ(1-42) at W5, after three immunizations, to the point that in five of the six dogs the peptide became undetectable (<3.125 pg/ml; Table 4A; FIG. 3A). The peptide concentration was maintained undetectable up to W13; experimented an increase at W31, four month after the seventh immunization when antibody titers were close to pre-immune levels; and then went down again after the booster (e) injection at W42 (FIG. 1). The magnitude of these changes is reflected in Table 5A. A little surprisingly, the plasma concentration of Aβ1-40 appeared to follow a pattern of changes very similar to Aβ (1-42) (Tables 4B and 5B, FIG. 3B). The correspondence between antibody titers and peptide concentration at any time point is represented in FIG. 4.

In spite of the substantial differences between group C and D regarding plasma antibody titers at any time point during the experiment, the fluctuation of Aβ peptide concentrations followed a similar time course. This suggests that even high antibody titers were not enough to achieve the clearance of Aβ peptides from the circulation.

Example 2

Immunization with Aβ(x-40) Peptide

I. Materials and Methods

1. Characteristics of the Animals

Six aged Beagles dogs of either sex were used in this invention. They came from commercial sources and had been living in the kennels of the University of Santiago for breeding. During the experiment, the animals were housed in three collective kennels with free indoor/outdoor access and were supplied with a formulated dog food and water ad libitum. The animals were thoroughly recognized just before the beginning of the experiments, including physical and neurological examination, blood biochemistry values and hemogram, and were declared healthy.

The animals were allocated in two groups (A and B; n=3) by a veterinary clinician blinded to the treatment eventually assigned to each group. The animals were explored every week for the apparition of any clinical sign of reaction to the vaccines. An additional complete recognition including again blood biochemistry and hemogram was carried out after the third immunization.

The animals were treated according to the European and Spanish legislations on animal handling (86/609/EU, Real Decreto 1201/2005) and every effort was done to minimize the suffering of the animals. The study was approved by the Ethical Committee of the University of Santiago.

2. Preparation of the Immunogens

A synthetic Aβ (33-40) peptide (with an additional N-terminal Cys when conjugated via SPDP) as antigen (0.4 mg/injection) incorporated in two different vaccine formulations, was used for the immunization of the animals. Each of these formulation combined a protein carrier, either blue carrier (BC; Pierce, Rockford, Ill.; group A) or bovine serum albumin (BSA; Sigma, Madrid, Spain; group B); and the adjuvant Abisco-300 (AB; Isconova AB, Uppsala Science Park, SE-751 83 Uppsala, SWEDEN).

The same procedure as in Example 1 (see Materials and methods, item 2.1) was used for conjugation of the peptides containing N-terminal cysteine to Blue Carrier and albumin with SPDP.

The two different formulations used in this invention were as follow:

(A) 400 micrograms of synthetic peptide conjugated to Blue Carrier plus 200 microliters of Abisco-300.
(B) 400 micrograms of synthetic peptide conjugated to BSA plus 37 microliters of Abisco-300.
The synthetic peptides used were:
When conjugated with SPDP:
Aβcys-(33-40) (NH$_2$—CGLMVGGVV-COOH) (SEQ ID NO:19) in rabbits (see below)

3. Immunizing Protocol and Blood Sampling

Animals were separated in 2 groups and assigned to any of the two vaccine formulations (See above (A) and (B)). Animals were immunized subcutaneously in the back and monitored for adverse reactions. The schedule for immunization and sampling is represented in FIG. 1 (B). Briefly, the animals were injected biweekly for seven times.

Blood samples were collected from the jugular vein into polypropylene vials with EDTA and protease inhibitors (complete mini mg/10 ml, Roche) just before the first immunization (W0), and a week after (W1), at week 5 (W5), at week 7 (W7), at week 9 (W9), at week 11 (W11) and at week 13 (W13) after the first immunization (FIG. 1 (B)).

The samples were gently mixed and preserved at 4° C. for a maximum of 2 hours before centrifugation at 4000 g during 10 minutes. Then the plasma was aliquoted and frozen at −80° C. until used. Additionally, in each extraction, ~1 ml of blood from every animal was collected in an EDTA-free polypropylene vial for obtaining the serum. This sample was allowed to clot for one hour at room temperature, then centrifuged at 4000 g 10 minutes and the serum collected and preserved at −80° C. until essayed for blood biochemistry determinations.

Samples of cerebrospinal fluid (CSF) were collected under general anesthesia and aseptic conditions a week before the first (W0) and at week 13$^{th}$ (W13), after the seventh immunization (FIG. 1 (B)). These CSF samples were aliquoted and frozen at −80° C. until used.

4. Anti-Aβ-Antibodies Assays in Plasma and CSF

Anti Aβ-antibodies were determined by direct ELISA in 96 wells polypropylene plates. Microtiter wells were coated with 2.5 µg/ml of human Aβ(1-40) peptide (#24224 AnaSpec. San Jose, Calif., USA) in 100 mM sodium bicarbonate and 2M guanidine hydrochloride buffer (pH 9.6) at 4° C. overnight. The plates were then washed three times with 300 µl of washing buffer (0.5 M Tris, 1.5 M sodium chloride, 0.5% Tween20; pH 8); blocked with 300 µl of blocking buffer (0.05 M Tris, 0.2% Tween20, 0.5% BSA; pH 8) for two hours at 37° C. and washed again another three times. The coated plates were incubated for one hour at 37° C. with 100 µl of three fold serial dilutions of the dog plasmas in vehicle buffer (0.05 M Tris, 0.5 M sodium chloride, 0.05% BSA, 0.05% Tween20; pH 8) in a row of 10 wells starting with a 1:30 dilution of the plasma in the first well. The greatest plasma dilution assayed was 1/10×3$^{10}$. The eleventh and twelfth column in each plate was filled with vehicle buffer without plasma for the blank controls. Then the plates were washed and incubated for one hour at 37° C. with 100 µl of a 1:1000 dilution in vehicle buffer of a horse radix peroxidase-conjugated rabbit anti-dog IgG (Jackson ImmunoResearch. Suffolk, UK), washed three times, and incubated with 0.0375% of ABTS (Roche, Barcelona, Spain) in buffer for ABTS (Roche. Barcelona, Spain). The absorbance at 405 nm was read on an automated plate reader (Synergy 4, Biotek. Winooski, Vt., USA).

Plasma anti-Aβ antibody concentrations were calculated using the monoclonal 6E10 antibody as a standard on the same ELISA plates and are expressed in µg/µl. The EC50 of each plasma sample was determined by the nonlinear regression of the absorbance to the logarithm of the dilutions in each well (GraphPad Prism 3.02). In addition, the plasma end-point titer was defined as the maximal plasma dilution in which absorbance was three times higher than the mean absorbance of the blank wells.

Determination of Free Aβ Peptides in Plasma

Levels of Aβ 1-42 and Aβ 1-40 in the plasma and CSF of the dogs were measured using indirect sandwich ELISA with the ABtest-40 and ABtest-42 ELISA kits from Araclon Biotech (Zaragoza, Spain) following the instructions of the manufacturer.

II. Results

The animals remained healthy and active throughout the whole time of the experiment. In particular, no sign of reaction to the vaccines was detected.

1. Anti-Aβ(1-40)Antibody Titers

Figure 5:
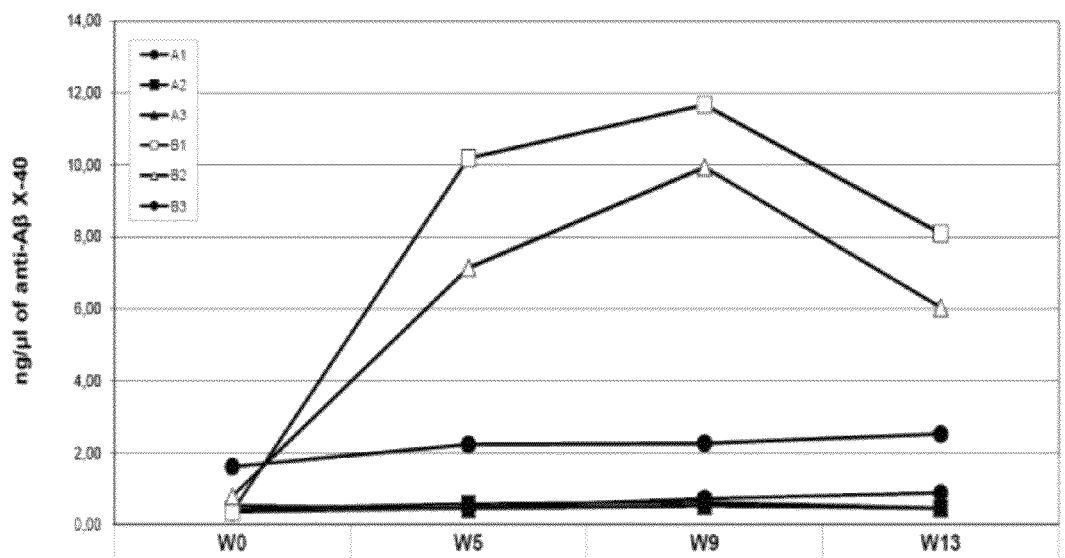
FIG. 5. Evolution of the plasma anti-Aβ 33-40 antibody titers. A) The anti-Aβ antibody titers of the plasma samples are expressed as equivalent to ng/gl of the anti-Aβ 40 (SAR 22) antibody. B) The anti-Aβ antibody titers of the plasma samples are expressed by their EC50. The different time points (in weeks) are represented in the horizontal axis. Each line represents one animal as indicated in the legend (A1-A3 in black and B1-B3 in white). Each of the two groups (A and B) received a different vaccine formulation.
Figure 5:
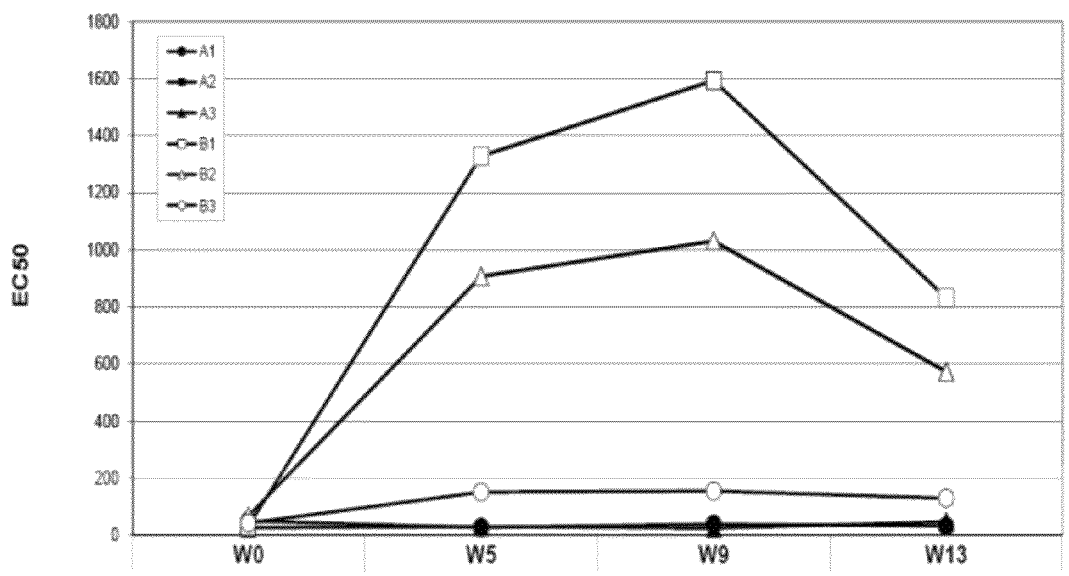

The dogs treated with the vaccine formulation B was more effective, showing substantial modifications in their plasma anti Aβ40 antibody titers. The response of all the dogs in this group, as measured by the concentration of anti Aβ40 antibody and the EC$_{50}$ or end-point dilution, followed the same pattern although quantitative differences were observed both, inter- and intra-groups (Table 6, Panels A-B). The general pattern in the dogs treated with the B formulation was characterized by a substantial increase of the titers after two immunizations (W5) that were maintained with only slight modifications from W5 to W9 (FIG. 5A). Thus, antibody titers were substantially increased after two immunizations but did not increase and even slightly decreased after the subsequent vaccine injections, specifically, after the seventh immunization (W13) the titers had slightly fallen to levels lower than W5 values (Table 6 and FIG. 5A) in group B.

TABLE 6

Plasma titers of specific anti-Aβ40 antibodies at different points

| Group/Dog | W0 | W5 | W9 | W13 |
|---|---|---|---|---|
| PANEL A: Equivalent to ng/µl of anti-Aβ40 antibody | | | | |
| A1 | 0.3483 | 0.4705 | 0.7251 | 0.8830 |
| A2 | 0.4196 | 0.5876 | 0.6284 | 0.4501 |
| A3 | 0.5214 | 0.4450 | 0.5214 | 0.4603 |
| B1 | 0.3585 | 10.1860 | 11.6729 | 8.0932 |
| B2 | 0.7913 | 7.1359 | 9.9314 | 6.0361 |
| B3 | 1.6111 | 2.2272 | 2.2629 | 2.5175 |
| PANEL B: values of plasma EC50 for the specific antibody (anti-Aβ40) | | | | |
| A1 | 49.47 | 26.92 | 38.54 | 31.01 |
| A2 | n.d. | n.d. | n.d. | 14.97 |
| A3 | 25.2 | 29.84 | 24.14 | 46.67 |
| B1 | 31.44 | 1328 | 1593 | 831.1 |
| B2 | 66.85 | 906.8 | 1031 | 571.9 |
| B3 | 42.15 | 150.9 | 154 | 129.1 | n.d.: not detectable

2. Aβ Peptide Titers

The dogs treated with the vaccine formulation B showed substantial modifications in their plasma Aβ (1-42) concentrations. These changes followed a pattern characterized by a substantial decrease of the Aβ (1-42) peptide at W5, after two immunizations, to the point that the peptide became undetectable (<3.125 pg/ml; Table 7A). The peptide concentration was maintained undetectable up to W13. However, dogs treated with the vaccine formulation A did not show any modifications in their plasma Aβ (1-42) concentrations. The plasma concentration of Aβ1-40 peptide appeared to follow a pattern of changes very similar to Aβ (1-42) (Table 7B).

After comparing the levels of CSF before immunization (W0) and in W13 in ELISA, the Aβ1-40 and Aβ(1-42) peptide levels decreased in animals from both groups (A and B) after the treatment with the vaccine. Surprisingly, the levels were even lower in dogs from group A than in dogs from group B, though dogs from group A did not present in an immunogenic response.

TABLE 7A

Concentration of peptide Aβ1-42 in pg/ml.

| Group/dog | W0 | W1 | W5 | W7 | W9 | W11 | W13 | CSF W0 | CSF W13 |
|---|---|---|---|---|---|---|---|---|---|
| A1 | <3.125 | <3.125 | <3.125 | <3.125 | 13.28 | 12.00 | 13.60 | 464.35 | 441.77 |
| A2 | 10.64 | 11.49 | 13.19 | 10.08 | 15.17 | 12.62 | 15.17 | 349.84 | 160.32 |
| A3 | 17.15 | 14.60 | 14.04 | 14.60 | 15.17 | 18.85 | 15.74 | 345.00 | 196.61 |
| B1 | 17.43 | 23.81 | <3.125 | <3.125 | <3.125 | <3.125 | <3.125 | 403.06 | 237.74 |
| B2 | 30.19 | 18.38 | <3.125 | <3.125 | <3.125 | <3.125 | <3.125 | 263.55 | 195.81 |
| B3 | <3.125 | 12.34 | <3.125 | <3.125 | <3.125 | <3.125 | <3.125 | 261.13 | 200.65 |

TABLE 7B

Concentration of peptide Aβ1-40 in pg/ml.

| Group/dog | W0 | W1 | W5 | W7 | W9 | W11 | W13 | CSF W0 | CSF W13 |
|---|---|---|---|---|---|---|---|---|---|
| A1 | 47.89 | 47.70 | 49.95 | 49.01 | 50.14 | 52.01 | 54.64 | 2576.97 | 2053.48 |
| A2 | 48.56 | 47.36 | 40.16 | 40.76 | 42.36 | 45.56 | 48.36 | 2734.55 | 1414.09 |
| A3 | 37.76 | 44.96 | 40.36 | 45.36 | 50.76 | 42.76 | 49.16 | 2616.36 | 1393.64 |
| B1 | 59.33 | 51.08 | <3.125 | <3.125 | <3.125 | <3.125 | <3.125 | 2752.73 | 2363.33 |
| B2 | 67.20 | 52.20 | <3.125 | <3.125 | <3.125 | <3.125 | <3.125 | 1665.61 | 1042.88 |
| B3 | 46.36 | 44.56 | <3.125 | <3.125 | <3.125 | <3.125 | <3.125 | 1831.52 | 1676.97 |

Example 3

Effect of Immunization in the Brain

I. Materials and Methods

To study the effect of immunization in the brain an acute experiment was carried out, in which the animals were sacrificed after three immunizations with the following formulations:

AβX-42+BSA+Th2-type adjuvant(Rehydragel). (1)

AβX-42+BSA+mixed Th1/Th2-type adjuvant (Abisco). (2)

Control: albumin+Th2-type adjuvant. (3)

Samples of the frontal, entorhinal, temporal and cerebellar brain regions were homogenized in TBS pH 7.4 containing a cocktail of proteases inhibitor, followed by a centrifugation at 175000 g during 30 min at 4° C. in a Beckman MLA-55 rotor. The resultant supernatant was considered as the soluble fraction of each. Then, the pellet was re-homogenized in TBS-TX pH 7.4 containing a cocktail of proteases inhibitor and centrifuged again in the same conditions as previously. Again, the resultant pellet was re-homogenized in TBS-guanidinium chloride and incubated overnight at room temperature in a rotating stirrer, followed by a centrifugation at 13000 g during 1 h30 min at 4° C. in a Beckman MLA-55 rotor. The pellet was discarded and the resultant supernatant was resuspended in TBS-guanidinium chloride and is considered as the insoluble fraction. The peptides concentration was then quantified by ELISA.

II. Results

Figure 6:
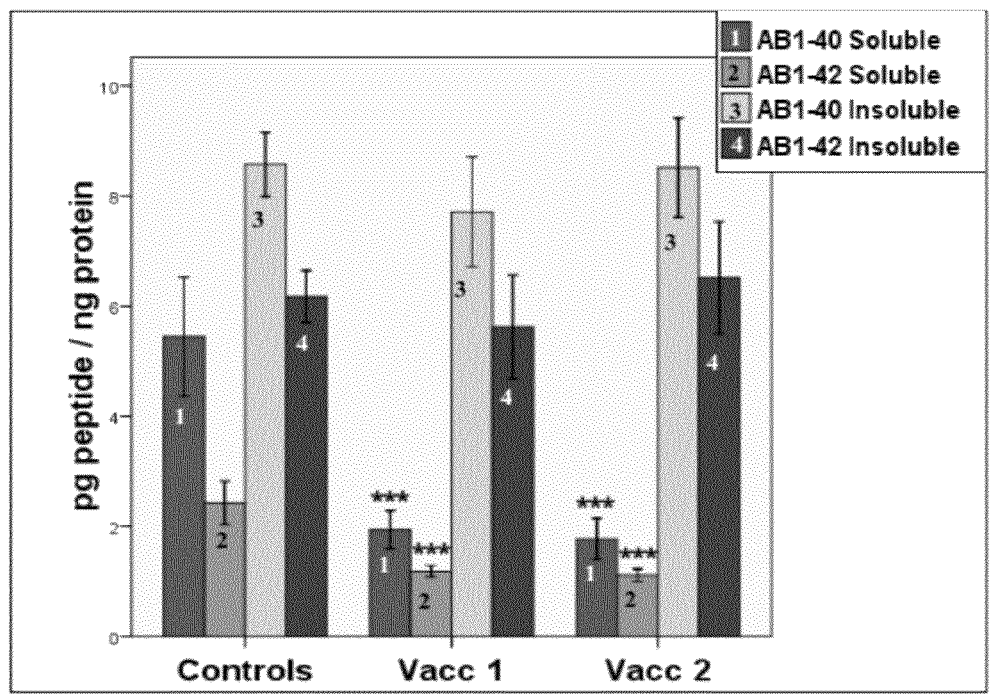
FIG. 6 is a graph showing the peptide concentration in the soluble form or in the insoluble form in the two groups of vaccination, compared to the control group. Vacc. 1 corresponds to Aβ X-42+BSA+Th2-type adjuvant and Vacc. 2 corresponds to Aβ X-42+BSA+mixed Th1/Th2-type adjuvant. Column (1) corresponds to Aβ 1-40 soluble form; (2) to Aβ 1-42 soluble form; (3) to Aβ 1-40 insoluble form and (4) to Aβ1-42 insoluble form.
Figure 7:
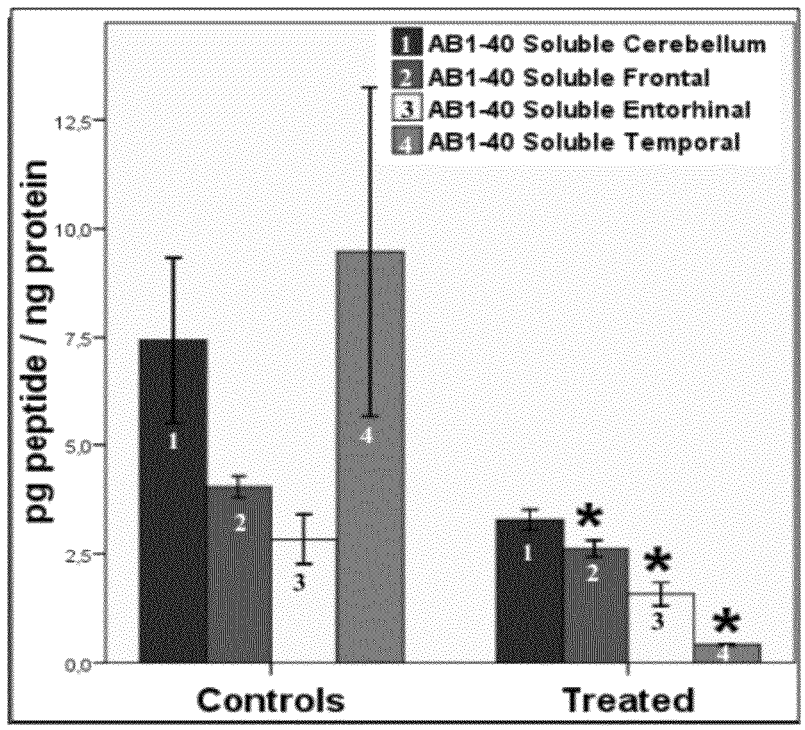
FIG. 7 is a graph showing the peptide concentration in the soluble form of the vaccinated groups, compared to the control group. (A) corresponds to soluble Aβ 1-40 peptides and (B) to soluble Aβ 1-42 peptides, whereas (1) indicates cerebellum sample; (2) frontal; (3) entorhinal and (4) temporal brain areas.
Figure 7:
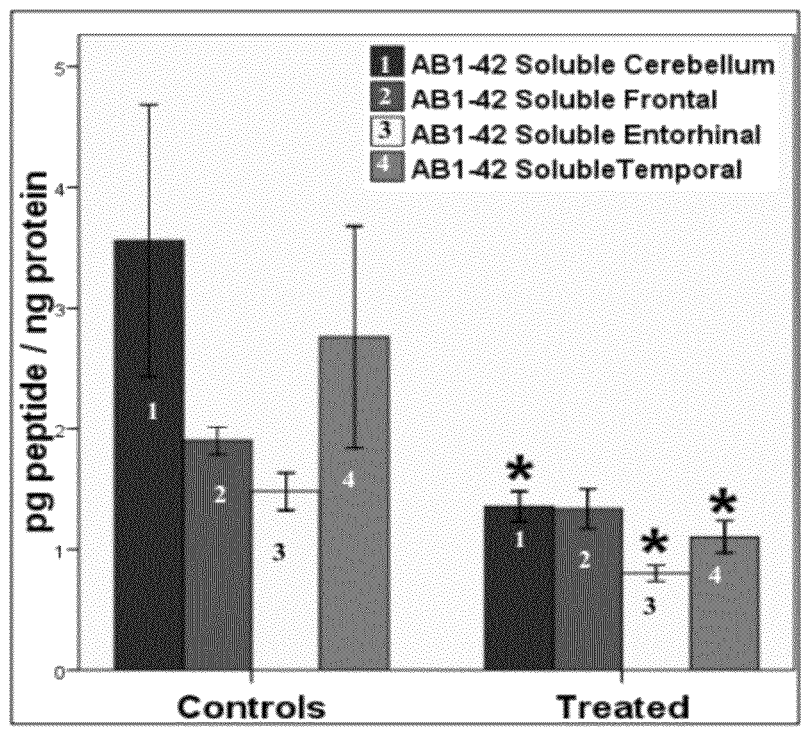

The immunization with Aβ X-42 conjugated to BSA results in a strong effect on the soluble form of the peptides, with a decrease in the concentration over 50% in each treated group with regard to the control group. The concentration in the insoluble form did not significantly decrease (FIG. 6). Regarding the different brain sections, the decrease was similar in all regions for the soluble form of Aβ40 and Aβ 42 peptides, with slight differences (FIG. 7).

As occurred in Examples 2 and 3, there were no differences in the peptide concentration in CSF comparing base line and post treatment time point.

The results obtained in this invention are congruent with the extended idea that Aβ immunization might be more efficient if administered before Aβ aggregation takes place.

The invention claimed is:

1. A conjugate consisting of a) a bovine serum albumin (BSA) directly connected to b) one or more than one linker region, each linker region directly connected to c) only one cysteine, wherein said cysteine is directly connected to d) the N-terminus of a single Amyloid β(35-42) peptide consisting of the amino acid sequence set forth in SEQ ID NO: 2 or a single Amyloid β(33-40) peptide consisting of the amino acid sequence set forth in SEQ ID NO: 4, wherein in said conjugate, said single Amyloid β peptide is connected through the one cysteine to said one linker region wherein said linker region is between said one cysteine and said BSA, and said conjugate terminates at the carboxy-terminus of the Amyloid β(35-42) peptide consisting of the amino acid sequence set forth in SEQ ID NO: 2 or Amyloid β(33-40) peptide consisting of the amino acid sequence set forth in SEQ ID NO: 4.

2. The conjugate of claim 1, wherein the cysteine is directly connected to said Amyloid β(35-42) peptide consisting of the amino acid sequence set forth in SEQ ID NO: 2.

3. The conjugate of claim 1, wherein the cysteine is directly connected to said Amyloid β(33-40) peptide consisting of the amino acid sequence set forth in SEQ ID NO: 4.

4. A pharmaceutical composition comprising the conjugate of claim 1 and an adjuvant.

5. A pharmaceutical composition comprising the conjugate of claim 2 and an adjuvant.

6. A pharmaceutical composition comprising the conjugate of claim 3 and an adjuvant.

* * * * *

UNITED STATES PATENT AND TRADEMARK OFFICE
CERTIFICATE OF CORRECTION

Page 1 of 1

PATENT NO.      : 9,023,991 B2
APPLICATION NO. : 13/322417
DATED           : May 5, 2015
INVENTOR(S)     : J. Manuel Sarasa Barrio It is certified that error appears in the above-identified patent and that said Letters Patent is hereby corrected as shown below:

On the title page, item (73) should read as follows:

Araclon Biotech, S.L., Zaragoza (ES)

Signed and Sealed this
Twenty-seventh Day of October, 2015

Michelle K. Lee
*Director of the United States Patent and Trademark Office*

SEQUENCE LISTING

<160> NUMBER OF SEQ ID NOS: 19

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

-continued

```
<210> SEQ ID NO 2
<211> LENGTH: 8
<212> TYPE: PRT
<213> ORGANISM: Homo sapiens

<400> SEQUENCE: 2

Met Val Gly Gly Val Val Ile Ala
1               5

<210> SEQ ID NO 3
<211> LENGTH: 10
<212> TYPE: PRT
<213> ORGANISM: Homo sapiens

<400> SEQUENCE: 3

Gly Leu Met Val Gly Gly Val Val Ile Ala
1               5                   10

<210> SEQ ID NO 4
<211> LENGTH: 8
<212> TYPE: PRT
<213> ORGANISM: Homo sapiens

<400> SEQUENCE: 4

Gly Leu Met Val Gly Gly Val Val
1               5

<210> SEQ ID NO 5
<211> LENGTH: 609
<212> TYPE: PRT
<213> ORGANISM: Homo sapiens

<400> SEQUENCE: 5

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205
```

```
Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu
```

```
<210> SEQ ID NO 6
<211> LENGTH: 607
<212> TYPE: PRT
<213> ORGANISM: Bos taurus

<400> SEQUENCE: 6
```

| | | | | | | | | | | | | | | | |
|---|---|---|---|---|---|---|---|---|---|---|---|---|---|---|---|
| Met | Lys | Trp | Val | Thr | Phe | Ile | Ser | Leu | Leu | Leu | Phe | Ser | Ser | Ala |
| 1 | | | | 5 | | | | | 10 | | | | | 15 |
| Tyr | Ser | Arg | Gly | Val | Phe | Arg | Arg | Asp | Thr | His | Lys | Ser | Glu | Ile | Ala |
| | | | 20 | | | | | 25 | | | | | 30 | | |
| His | Arg | Phe | Lys | Asp | Leu | Gly | Glu | Glu | His | Phe | Lys | Gly | Leu | Val | Leu |
| | | | 35 | | | | 40 | | | | | 45 | | | |
| Ile | Ala | Phe | Ser | Gln | Tyr | Leu | Gln | Gln | Cys | Pro | Phe | Asp | Glu | His | Val |
| | 50 | | | | | 55 | | | | | 60 | | | | |
| Lys | Leu | Val | Asn | Glu | Leu | Thr | Glu | Phe | Ala | Lys | Thr | Cys | Val | Ala | Asp |
| 65 | | | | | 70 | | | | | 75 | | | | | 80 |
| Glu | Ser | His | Ala | Gly | Cys | Glu | Lys | Ser | Leu | His | Thr | Leu | Phe | Gly | Asp |
| | | | | 85 | | | | | 90 | | | | | 95 | |
| Glu | Leu | Cys | Lys | Val | Ala | Ser | Leu | Arg | Glu | Thr | Tyr | Gly | Asp | Met | Ala |
| | | | 100 | | | | | 105 | | | | | 110 | | |
| Asp | Cys | Cys | Glu | Lys | Gln | Glu | Pro | Glu | Arg | Asn | Glu | Cys | Phe | Leu | Ser |
| | | | 115 | | | | | 120 | | | | | 125 | | |
| His | Lys | Asp | Asp | Ser | Pro | Asp | Leu | Pro | Lys | Leu | Lys | Pro | Asp | Pro | Asn |
| | 130 | | | | | 135 | | | | | 140 | | | | |
| Thr | Leu | Cys | Asp | Glu | Phe | Lys | Ala | Asp | Glu | Lys | Lys | Phe | Trp | Gly | Lys |
| 145 | | | | | 150 | | | | | 155 | | | | | 160 |
| Tyr | Leu | Tyr | Glu | Ile | Ala | Arg | Arg | His | Pro | Tyr | Phe | Tyr | Ala | Pro | Glu |
| | | | | 165 | | | | | 170 | | | | | 175 | |
| Leu | Leu | Tyr | Tyr | Ala | Asn | Lys | Tyr | Asn | Gly | Val | Phe | Gln | Glu | Cys | Cys |
| | | | 180 | | | | | 185 | | | | | 190 | | |
| Gln | Ala | Glu | Asp | Lys | Gly | Ala | Cys | Leu | Leu | Pro | Lys | Ile | Glu | Thr | Met |
| | | | 195 | | | | | 200 | | | | | 205 | | |
| Arg | Glu | Lys | Val | Leu | Ala | Ser | Ser | Ala | Arg | Gln | Arg | Leu | Arg | Cys | Ala |
| | 210 | | | | | 215 | | | | | 220 | | | | |
| Ser | Ile | Gln | Lys | Phe | Gly | Glu | Arg | Ala | Leu | Lys | Ala | Trp | Ser | Val | Ala |
| 225 | | | | | 230 | | | | | 235 | | | | | 240 |
| Arg | Leu | Ser | Gln | Lys | Phe | Pro | Lys | Ala | Glu | Phe | Val | Glu | Val | Thr | Lys |
| | | | | 245 | | | | | 250 | | | | | 255 | |
| Leu | Val | Thr | Asp | Leu | Thr | Lys | Val | His | Lys | Glu | Cys | Cys | His | Gly | Asp |
| | | | 260 | | | | | 265 | | | | | 270 | | |
| Leu | Leu | Glu | Cys | Ala | Asp | Asp | Arg | Ala | Asp | Leu | Ala | Lys | Tyr | Ile | Cys |
| | | | 275 | | | | | 280 | | | | | 285 | | |
| Asp | Asn | Gln | Asp | Thr | Ile | Ser | Ser | Lys | Leu | Lys | Glu | Cys | Cys | Asp | Lys |
| | 290 | | | | | 295 | | | | | 300 | | | | |
| Pro | Leu | Leu | Glu | Lys | Ser | His | Cys | Ile | Ala | Glu | Val | Glu | Lys | Asp | Ala |
| 305 | | | | | 310 | | | | | 315 | | | | | 320 |
| Ile | Pro | Glu | Asn | Leu | Pro | Pro | Leu | Thr | Ala | Asp | Phe | Ala | Glu | Asp | Lys |
| | | | | 325 | | | | | 330 | | | | | 335 | |
| Asp | Val | Cys | Lys | Asn | Tyr | Gln | Glu | Ala | Lys | Asp | Ala | Phe | Leu | Gly | Ser |
| | | | 340 | | | | | 345 | | | | | 350 | | |
| Phe | Leu | Tyr | Glu | Tyr | Ser | Arg | Arg | His | Pro | Glu | Tyr | Ala | Val | Ser | Val |
| | | | 355 | | | | | 360 | | | | | 365 | | |
| Leu | Leu | Arg | Leu | Ala | Lys | Glu | Tyr | Glu | Ala | Thr | Leu | Glu | Glu | Cys | Cys |
| | 370 | | | | | 375 | | | | | 380 | | | | |

```
Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
            405                 410                 415

Gln Phe Glu Lys Leu Gly Glu Tyr Gly Phe Gln Asn Ala Leu Ile Val
            420                 425                 430

Arg Tyr Thr Arg Lys Val Pro Gln Val Ser Thr Pro Thr Leu Val Glu
            435                 440                 445

Val Ser Arg Ser Leu Gly Lys Val Gly Thr Arg Cys Cys Thr Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
            485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Val Pro Lys Ala Phe Asp Glu Lys
            515                 520                 525

Leu Phe Thr Phe His Ala Asp Ile Cys Thr Leu Pro Asp Thr Glu Lys
            530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
            565                 570                 575

Phe Val Asp Lys Cys Cys Ala Ala Asp Asp Lys Glu Ala Cys Phe Ala
            580                 585                 590

Val Glu Gly Pro Lys Leu Val Val Ser Thr Gln Thr Ala Leu Ala
            595                 600                 605

<210> SEQ ID NO 7
<211> LENGTH: 14
<212> TYPE: PRT
<213> ORGANISM: Artificial
<220> FEATURE:
<223> OTHER INFORMATION: SGGTSGSTSGTGST Linker region

<400> SEQUENCE: 7

Ser Gly Gly Thr Ser Gly Ser Thr Ser Gly Thr Gly Ser Thr
1               5                   10

<210> SEQ ID NO 8
<211> LENGTH: 15
<212> TYPE: PRT
<213> ORGANISM: Artificial
<220> FEATURE:
<223> OTHER INFORMATION: AGSSTGSSTGPGSTT Linker

<400> SEQUENCE: 8

Ala Gly Ser Ser Thr Gly Ser Ser Thr Gly Pro Gly Ser Thr Thr
1               5                   10                  15

<210> SEQ ID NO 9
<211> LENGTH: 7
<212> TYPE: PRT
<213> ORGANISM: Artificial
<220> FEATURE:
<223> OTHER INFORMATION: GGSGGAP  Linker
```

```
<400> SEQUENCE: 9

Gly Gly Ser Gly Gly Ala Pro
1               5

<210> SEQ ID NO 10
<211> LENGTH: 8
<212> TYPE: PRT
<213> ORGANISM: Artificial
<220> FEATURE:
<223> OTHER INFORMATION: GGGKGGGG  Linker

<400> SEQUENCE: 10

Gly Gly Gly Lys Gly Gly Gly Gly
1               5

<210> SEQ ID NO 11
<211> LENGTH: 8
<212> TYPE: PRT
<213> ORGANISM: Artificial
<220> FEATURE:
<223> OTHER INFORMATION: GGGKGGGG Linker

<400> SEQUENCE: 11

Gly Gly Gly Lys Gly Gly Gly Gly
1               5

<210> SEQ ID NO 12
<211> LENGTH: 7
<212> TYPE: PRT
<213> ORGANISM: Artificial
<220> FEATURE:
<223> OTHER INFORMATION: GTKVHMK Linker

<400> SEQUENCE: 12

Gly Thr Lys Val His Met Lys
1               5

<210> SEQ ID NO 13
<211> LENGTH: 13
<212> TYPE: PRT
<213> ORGANISM: Artificial
<220> FEATURE:
<223> OTHER INFORMATION: PGTSGQQPSVGQQ Linker

<400> SEQUENCE: 13

Pro Gly Thr Ser Gly Gln Gln Pro Ser Val Gly Gln Gln
1               5                   10

<210> SEQ ID NO 14
<211> LENGTH: 5
<212> TYPE: PRT
<213> ORGANISM: Artificial
<220> FEATURE:
<223> OTHER INFORMATION: GTSGQ Linker

<400> SEQUENCE: 14

Gly Thr Ser Gly Gln
1               5

<210> SEQ ID NO 15
<211> LENGTH: 10
<212> TYPE: PRT
<213> ORGANISM: Artificial
<220> FEATURE:
<223> OTHER INFORMATION: PKPSTPPGSS Linker
```

```
<400> SEQUENCE: 15

Pro Lys Pro Ser Thr Pro Pro Gly Ser Ser
1               5                   10

<210> SEQ ID NO 16
<211> LENGTH: 11
<212> TYPE: PRT
<213> ORGANISM: Artificial
<220> FEATURE:
<223> OTHER INFORMATION: APAETKAEPMT Linker

<400> SEQUENCE: 16

Ala Pro Ala Glu Thr Lys Ala Glu Pro Met Thr
1               5                   10

<210> SEQ ID NO 17
<211> LENGTH: 9
<212> TYPE: PRT
<213> ORGANISM: Artificial
<220> FEATURE:
<223> OTHER INFORMATION: Human Abeta(35-42) with N-terminal Cys

<400> SEQUENCE: 17

Cys Met Val Gly Gly Val Val Ile Ala
1               5

<210> SEQ ID NO 18
<211> LENGTH: 11
<212> TYPE: PRT
<213> ORGANISM: Artificial
<220> FEATURE:
<223> OTHER INFORMATION: Human Abeta33-42 with N-terminal Cys

<400> SEQUENCE: 18

Cys Gly Leu Met Val Gly Gly Val Val Ile Ala
1               5                   10

<210> SEQ ID NO 19
<211> LENGTH: 9
<212> TYPE: PRT
<213> ORGANISM: Artificial
<220> FEATURE:
<223> OTHER INFORMATION: Cys-AB 33-40

<400> SEQUENCE: 19

Cys Gly Leu Met Val Gly Gly Val Val
1               5
```